US010010709B2

(12) United States Patent
Kohane et al.

(10) Patent No.: US 10,010,709 B2
(45) Date of Patent: Jul. 3, 2018

(54) COMPOSITION FOR ON-DEMAND ULTRASOUND-TRIGGERED DRUG DELIVERY

(75) Inventors: Daniel S. Kohane, Newton, MA (US); Hila Epstein-Barash, Newton, MA (US); Mark A. Borden, Boulder, CO (US)

(73) Assignees: THE TRUSTEES OF COLUMBIA UNIVERSITY IN THE CITY OF NEW YORK, New York, NY (US); MASSACHUSETTS INSTITUTE OF TECHNOLOGY, Cambridge, MA (US); CHILDREN'S MEDICAL CENTER CORPORATION, Boston, MA (US)

(*) Notice: Subject to any disclaimer, the term of this patent is extended or adjusted under 35 U.S.C. 154(b) by 1522 days.

(21) Appl. No.: 13/515,764

(22) PCT Filed: Dec. 16, 2010

(86) PCT No.: PCT/US2010/060691
§ 371 (c)(1),
(2), (4) Date: Oct. 26, 2012

(87) PCT Pub. No.: WO2011/075557
PCT Pub. Date: Jun. 23, 2011

(65) Prior Publication Data
US 2013/0041311 A1 Feb. 14, 2013

Related U.S. Application Data

(60) Provisional application No. 61/287,159, filed on Dec. 16, 2009.

(51) Int. Cl.
*A61M 37/00* (2006.01)
*A61K 9/00* (2006.01)
(Continued)

(52) U.S. Cl.
CPC ....... *A61M 37/0069* (2013.01); *A61K 9/0009* (2013.01); *A61K 9/107* (2013.01);
(Continued)

(58) Field of Classification Search
CPC . A61M 37/0069; A61K 9/107; A61K 9/0009; A61K 41/0028; A61L 2300/62; A61L 2300/602
See application file for complete search history.

(56) References Cited

U.S. PATENT DOCUMENTS

| 3,598,111 A | 8/1971 | Kahn et al. |
| 4,440,921 A | 4/1984 | Allcock et al. |

(Continued)

FOREIGN PATENT DOCUMENTS

| WO | WO 99/39738 A1 | 8/1999 |
| WO | WO 2010044385 | 4/2010 |
| WO | WO 2010063951 | 6/2010 |

OTHER PUBLICATIONS

Duck, "Physical properties of tissue: a comprehensive reference book. 1990 Academic Press," London, UK.
(Continued)

*Primary Examiner* — Bradley J Osinski
(74) *Attorney, Agent, or Firm* — Potomac Law Group, PLLC; Mark Catan

(57) ABSTRACT

Injectable or implantable drug delivery systems providing on-demand ultrasound-triggered drug release and methods for controlling the release of drug in a patient are provided herein. The on-demand drug delivery systems contain a drug depot and a drug encapsulated in an encapsulating material, where the encapsulating material is different from the depot. In the preferred embodiment, the depot also contains microbubbles that encapsulate one or more gases. The microbubbles enhance the drug release when ultrasound is
(Continued)

applied compared to the same system in the absence of microbubbles. In a preferred embodiment, the drug delivery system, contains an encapsulating material, preferably liposomes, a drug to be delivered, microbubbles, and at least two hydrogel-forming precursor components. Following injection or implantation, the patient can control the time, location and dosage released by administering ultrasound.

14 Claims, 7 Drawing Sheets

(51) Int. Cl.
  *A61K 9/107* (2006.01)
  *A61K 41/00* (2006.01)
  *A61K 9/06* (2006.01)
(52) U.S. Cl.
  CPC ............ *A61K 41/0028* (2013.01); *A61K 9/06* (2013.01); *A61L 2300/602* (2013.01); *A61L 2300/62* (2013.01); *A61L 2300/626* (2013.01); *A61L 2400/06* (2013.01); *A61M 37/0092* (2013.01)

(56) References Cited

U.S. PATENT DOCUMENTS

| | | | |
|---|---|---|---|
| 4,495,174 | A | 1/1985 | Allcock et al. |
| 4,757,128 | A | 7/1988 | Domb et al. |
| 4,777,599 | A | 10/1988 | Dorogi et al. |
| 4,789,724 | A | 12/1988 | Domb et al. |
| 4,857,311 | A | 8/1989 | Domb et al. |
| 4,880,622 | A | 11/1989 | Allcock et al. |
| 4,888,176 | A | 12/1989 | Langer et al. |
| 4,946,938 | A | 8/1990 | Magill et al. |
| 5,107,837 | A | 4/1992 | Ophir et al. |
| 5,178,147 | A | 1/1993 | Ophir et al. |
| 5,309,914 | A | 5/1994 | Iinuma |
| 5,435,310 | A | 7/1995 | Sheehan et al. |
| 5,601,084 | A | 2/1997 | Sheehan et al. |
| 5,606,971 | A | 3/1997 | Sarvazyan |
| 5,662,113 | A | 9/1997 | Liu |
| 5,722,411 | A | 3/1998 | Suzuki et al. |
| 5,810,731 | A | 9/1998 | Sarvazyan et al. |
| 5,840,028 | A | 11/1998 | Chubachi et al. |
| 5,874,500 | A | 2/1999 | Rhee et al. |
| 5,928,151 | A | 7/1999 | Hossack et al. |
| 6,102,864 | A | 8/2000 | Hatfield et al. |
| 6,102,865 | A | 8/2000 | Hossack et al. |
| 6,123,669 | A | 9/2000 | Kanda |
| 6,241,675 | B1 | 6/2001 | Smith et al. |
| 6,246,895 | B1 | 6/2001 | Plewes |
| 6,312,382 | B1 | 11/2001 | Mucci et al. |
| 6,352,507 | B1 | 3/2002 | Torp et al. |
| 6,508,768 | B1 | 1/2003 | Hall et al. |
| 6,537,217 | B1 | 3/2003 | Bjærum et al. |
| 6,537,221 | B2 | 3/2003 | Criton et al. |
| 6,649,702 | B1* | 11/2003 | Rapoport ............ A61K 9/0009 424/486 |
| 6,671,541 | B2 | 12/2003 | Bishop et al. |
| 6,683,454 | B2 | 1/2004 | Rehwald et al. |
| 6,685,641 | B2 | 2/2004 | Liu |
| 6,875,176 | B2 | 4/2005 | Mourad et al. |
| 6,896,659 | B2 | 5/2005 | Conston et al. |
| 6,930,087 | B2 | 8/2005 | Baru et al. |
| 7,055,378 | B2 | 6/2006 | Su et al. |
| 7,257,244 | B2 | 8/2007 | Miga |
| 7,331,926 | B2 | 2/2008 | Varghese et al. |
| 7,421,101 | B2 | 9/2008 | Georgescu et al. |
| 7,601,122 | B2 | 10/2009 | Zagzebski et al. |
| 7,753,847 | B2 | 7/2010 | Greenleaf et al. |
| 8,029,444 | B2 | 10/2011 | Pedrizzetti et al. |
| 2002/0039594 | A1* | 4/2002 | Unger ............... A61K 9/0009 424/426 |
| 2002/0065461 | A1 | 5/2002 | Cosman |
| 2003/0220556 | A1 | 11/2003 | Porat et al. |
| 2004/0006266 | A1 | 1/2004 | Ustuner et al. |
| 2004/0059224 | A1 | 3/2004 | Varghese et al. |
| 2004/0092816 | A1 | 5/2004 | Ossmann et al. |
| 2004/0249580 | A1 | 12/2004 | Pourcelot et al. |
| 2005/0004466 | A1 | 1/2005 | Hynynen et al. |
| 2005/0054930 | A1 | 3/2005 | Rickets et al. |
| 2005/0059876 | A1 | 3/2005 | Krishnan et al. |
| 2005/0080336 | A1 | 4/2005 | Byrd et al. |
| 2005/0084538 | A1 | 4/2005 | Dayton et al. |
| 2005/0175541 | A1 | 8/2005 | Lanza et al. |
| 2005/0267695 | A1 | 12/2005 | German |
| 2006/0002994 | A1 | 1/2006 | Thomas et al. |
| 2006/0034904 | A1 | 2/2006 | Weimann |
| 2006/0058673 | A1 | 3/2006 | Aase et al. |
| 2006/0074315 | A1 | 4/2006 | Liang et al. |
| 2006/0173320 | A1 | 8/2006 | Radulescu |
| 2007/0049824 | A1 | 3/2007 | Konofagou et al. |
| 2007/0207194 | A1 | 9/2007 | Grayburn et al. |
| 2007/0219447 | A1 | 9/2007 | Kanai et al. |
| 2007/0276242 | A1 | 11/2007 | Konofagou |
| 2007/0276245 | A1 | 11/2007 | Konofagou |
| 2008/0194957 | A1 | 8/2008 | Hoctor et al. |
| 2008/0260802 | A1 | 10/2008 | Sawhney et al. |
| 2008/0269606 | A1 | 10/2008 | Matsumura |
| 2008/0285819 | A1 | 11/2008 | Konofagou et al. |
| 2011/0208038 | A1 | 8/2011 | Konofagou et al. |

OTHER PUBLICATIONS

Jensen et al., "Calculation of pressure fields from arbitrarily shaped, apodized, and excited ultrasound transducers," IEEE Transactions on Ultrasonics, Ferroelectrics and Frequency Control, vol. 39(2), pp. 262-267, Mar. 1992.
Mitri et al., "Chirp imaging vibro-acoustography for removing the ultrasound standing wave artifact," IEEE transactions on medical imaging, vol. 24(10), pp. 1249-1255, Oct. 2005.
Bers, "Cardiac excitation-contraction coupling", Nature, Jan. 10, 2002, vol. 415:198-205.
Ramanathan et al., (2004) "Noninvasive electrocardiographic imaging for cardiac electrophysiology and arrhythmia," Nat Med 10(4):422-428.
Berger et al., (2006) "Single-Beat Noninvasive Imaging of Cardiac Electrophysiology of Ventricular Pre-Excitation. Journal of the American College of Cardiology," 48(10):2045-2052.
Greenstein et al., (2006) "Mechanisms of Excitation-Contraction Coupling in an Integrative Model of the Cardiac Ventricular Myocyte," Biophysical Journal 90:77-91.
Rice et al., "Approximate model of cooperative activation and crossbridge cycling in cardiac muscle using ordinary differential equations," Biophys. J 95:2368-2390, Sep. 2008.
Campbell et al., "Mechanisms of transmurally varying myocyte electromechanics in an integrated computational model," Phl. Trans. R. Soc. A., 366:3361-3380, Jul. 1, 2008.
Gurev et al., "Distribution of Electromechanical Delay in the Heart: Insights from a Three-Dimensional Electromechanical Model," Biophysical Journal 99:745-754, Aug. 2010.
Badke et al., (1980) "Effects of ventricular pacing on regional left ventricular performance in the dog," Am J Physiol Heart Circ Physiol 238:H858-867.
Wyman et al., (1999) "Mapping propagation of mechanical activation in the paced heart with MRI tagging," Am J Physiol Heart Circ Physiol 276:H881-891.
Prinzen et al., (1992) "The time sequence of electrical and mechanical activation during spontaneous beating and ectopic stimulation," Eur Heart J 13:535-543.
Provost et al., (2010) "Electromechanical Wave Imaging of Normal and Ischemic Hearts in Vivo," IEEE Trans. Med. Imaging 29(3):625-635.
Shehata et al., (2009) "Myocardial tissue tagging with cardiovascular magnetic resonance," Journal of Cardiovascular Magnetic Resonance 11:55.

(56) References Cited

OTHER PUBLICATIONS

Pernot et al.,(2007) "ECG-gated, Mechanical and Electromechanical Wave Imaging of Cardiovascular Tissues in Vivo," Ultrasound in Medicine & Biology 33(7):1075-1085.
Provost et al., (2008) In 2008 IEEE International Ultrasonics Symposium (Beijing, China).
Durrer et al. (1970) "Total Excitation of the Isolated Human Heart. Circulation," 41:899-912.
Sengupta et al.,(2008) "Electromechanical activation sequence in normal heart," Heart Fail Clin. 4:303-14.
Scher et al., (1956) "The pathway of ventricular depolarization in the dog," Circ. Res 4:461-469.
Faris et al. (2003) "Novel Technique for Cardiac Electromechanical Mapping with Magnetic Resonance Imaging Tagging and an Epicardial Electrode Sock," Ann Biomed Eng. 31:430-440.
Gurev et al., (2009) "In silico characterization of ventricular activation pattern by electromechanical wave imaging," Supplement to Heart Rhythm 6:S357.
Ramanathan et al., "Activation and repolarization of the normal human heart under complete physiological conditions," Proceedings of the National Academy of Sciences 103(16):6309-6314, Apr. 18, 2006.
Lee et al., "Theoretical Quality Assessment of Myocardial Elastography with In Vivo Validation," Ultrasonics, Ferroelectrics and Frequency Control, IEEE Transactions on 54(1):2233-2245, Nov. 11, 2007.
Kimber et al. (1996) "A Comparison of Unipolar and Bipolar Electrodes During Cardiac Mapping Studies," Pacing Clin Electro 19:1196-1204.
Kallel et al., (1997) "A least-squares strain estimator for elastography," Ultrason Imaging 19:195-208.
Luo et al., "High-frame rate, full-view myocardial elastography with automated contour tracking in murine left ventricles in vivo," IEEE Transactions on Ultrasonics, Ferroelectrics and Frequency Control, 55(1):240-248, Jan. 2008.
Lai et al., (1993) "Introduction to Continuum Mechanics," (Pergamon Pr). 3rd Ed., Contents.
Stewart et al., "Blood-eye barriers in the rat: Correlation of ultrastructure with function," J. Comp. Neurol., vol. 340, No. 4, pp. 566-576, 1994.
Samuel et al., "An ex vivo study of the correlation between acoustic emission and microvascular damage," Ultrasound Med. Biol., vol. 35, No. 9, pp. 1574-1586, 2009.
Luo et al., "Pulse wave imaging of normal and aneurysmal abdominal aortas in vivo", IEEE Trans. Med. Imaging 28(4): 477-486, 2009.
Luo et al., "A fast normalized cross-correlation method for motion estimation," IEEE Trans. Ultrason. Ferroelectr. Control 57(6): 1347-1357, Jun. 2010.
Maleke et al., "Single-Element focused Ultrasound Transducer Method for Harmonic Motion Imaging," Ultrason. Imagin, vol. 28, No. 3, pp. 144-158, 2006.
Maleke et al., "In Vivo Feasibility of Real-time Monitoring of Focused Ultrasound Surgery (FUS) Using Harmonic Motion Imaging (HMI)," IEEE Trans. Biomed. Eng., vol. 57(1), pp. 7-11, Jan. 2010.
Vappou et al., "Quantitive Viscoelastic Parameters Measured by Harmonic Motion Imaging," Phys. Med. Biol., vol. 54, pp. 3579-3595, Mar. 2009.
Ophir et al., "Elastography: A quantitative method for imaging the elasticity of biological tissues," Ultrasonic Imaging, vol. 13(2), pp. 111-134, 1991.
Huang et al., "Watershed Segmentation for Breast Tumor in 2-D Sonography," May 2004, Ultrasound in Medicine and Biology, pp. 625-632.
Chang et al., "3-D US Frame Positioning Using Speckle Decorrelation and Image Registration," Jun. 2003, Ultrasound in Medicine and Biology, pp. 801-812.
Luo et al., "Myocardial elastography at both high temporal and spatial resolution for the detection of infarcts," Ultrasound in Med. & Bio, vol. 33(8), pp. 1206-1223, Aug. 2007.
Wang et al., "A composite high frame-rate system for clinical cardiovascular imaging," IEEE Transactions on Ultrasonics, Ferroelectrics, and Frequency Control, vol. 55(10), pp. 2221-2233, Oct. 2008.
Wang et al., "A composite imaging technique for high frame-rate and full-view cardiovascular ultrasound and elasticity imaging," IEEE International Ultrasonics Symposium, New York, NY, Oct. 28-31, 2007.
Kanai, "Propagations of spontaneously actuated pulsive vibration in human heart wall and in vivo viscoelasticity estimation," IEE Transaction on Ultrasonics, Ferroelectrics, and Frequency Control, vol. 52(11), pp. 1931-1942, Nov. 2005.
Bercoff et al., "Supersonic Shear Imaging: A new technique for soft tissue elasticity mapping," IEEE Transactions on Ultrasonics, Ferroelectrics, and Frequency Control, vol. 51(4), pp. 396-409, Apr. 2004.
McLaughlin et al., "Piezoelectric sensor determination of arterial pulse wave velocity," Physiol. Meas., vol. 24(3), pp. 693-702, 2003.
Greenwald, "Pulse pressure and arterial elasticity," QJM: An International Journal of Medicine, vol. 95(2), pp. 107-112, 2002.
Kanai et al., "Myocardial rapid velocity distribution," Ultrasound Med. & Biol., vol. 27(4), pp. 481-498, Apr. 2001.
Rogers et al., "Age-associated changes in regional aortic pulse wave velocity," J Am Coll. Cardiol., vol. 38(4), pp. 1123-1129, 2001.
Declerck et al., "Left ventricular motion reconstruction from planar tagged MR images: a comparison," Phys. Med. Biol., vol. 45(6), pp. 1611-1632, Jun. 2000.
Kanai et al., "Transcutaneous measurement of frequency dispersion in the regional pulse wave velocity," IEEE Ultrasonics Symposium, 2000.
Sinkus et al., "High-resolution tensor MR elastography for breast tumor reduction," Phys Med Biol, 2000, 45(6): 1649-1664.
Roth, "Influence of a perfusing bath on the foot of the cardiac action potential," Circulation Research, vol. 86, E19-E22, 2000.
Wang et al., "Increased aortic stiffness assessed by pulse wave velocity in apolipoprotein E-deficient mice," Am J Physiol Heart Circ. Physiol., vol. 278, No. 2, pp. H428-H434, 2000.
Sandrin et al., "Time-resolved pulsed elastography with ultrafast ultrasonic imaging," Ultrason Imaging, vol. 21(4), pp. 259-272, 1999.
Cutnell et al., Physics, Fourth Edition, New York. Table of Contents, 1998.
Heimdal et al., "Real-time strain rate imaging of the left ventricle by ultrasound," J Am Soc. Echocardiog., vol. 11(11), pp. 1013-1019, 1998.
Konofagou et al., "A New Elastographic Method for Estimation and Imaging od Lateral Strains, Corrected Axial Strains and Poison's Ratios in Tissues," Ultrasound in Medicine & Biology 24(8): 1183-1199, 1998.
Konofagou et al., "Three-dimensional Motion estimation in Elastography," IEEE Proceedings of the Symposium of Ultrasonics, Ferroelectrics, and Frequency Control in Sendai Japan, pp. 1745-1748, vol. 2, 1998.
Nichols et al., "Vascular Impedance. In McDonald's: blood flow in arteries: theoretical, experimental, and clinical principles," E Arnold, London, 1998. Table of Contents.
Sarvazyan et al., "Shear wave elasticity imaging: A new ultrasonic technology of medical diagnostics," Ultrasound Med Biol, vol. 24(9), pp. 1419-1435, Nov. 1998.
Spach et al., "Extracellular discontinuities in cardiac muscle—Evidence for capillary effects on the action potential foot," Circulation Research, vol. 83, pp. 1144-1164, 1998.
Sutherland, "Color Doppler Myocardial Imaging—Potential Applications in Acquired and Congenital Heart Disease," Acta Paediatr, 84: pp. 40-48, Aug. 1995.
Walker et al., "A Fundamental Limit on Delay Estimation Using Partially Correlated Speckle Signals," IEEE T Ultrason Ferr, vol. 42(2), pp. 301-308, Mar. 1995.

(56) References Cited

OTHER PUBLICATIONS

Gupta, et al., "Changes in Passive mechanical Stiffness of Myocardial Tissue with Aneurysm Formation," Circulation, vol. 89, pp. 2315-2326, 1994.
Fung, "Biomechanics—Mechanical Properties of Living Tissues," New York, 1993, Table of Contents.
Kanai, et al., "A New Method for Measuring Small Local Vibrations in the Heart Using Ultrasound," IEEE T Bio-Med Eng, vol. 40(12), pp. 1233-1242, Dec. 1993.
Zerhouni, et al., "Human Heart: tagging with MR imaging—a method for noninvasive assessment of myocardial motion," Radiology 169(1): 59-63, Oct. 1988.
Bonnefous, et al., "Time domain formulation of pulse-Doppler ultrasound and blood velocity estimation by cross-correlation," Ultrason Imaging, vol. 8(2), pp. 73-85, Apr. 1986.
Avolio, et al., "Effects of aging on changing arterial compliance and left ventricular load in a northern Chinese urban community," Circulation, vol. 68(1), pp. 50-58, 1983.
Edwards, et al., "Effects of Ischemia on Left-Ventricular Regional Function in the Conscious Dog," American Journal of Physiology, vol. 240, pp. H413-H420, 1981.
Henderson, et al., "Series Elasticity of Heart Muscle During Hypoxia," Cardiovascular Research, vol. 5, pp. 10-14, 1971.
Konofagou et al., "Myocardial Elastography—Feasibility Study in Vivo," Ultrasound Med & Biol, vol. 28(4), pp. 475-482, Apr. 2002.
McNally et al., "Computer Vision Elastography: Speckle Adaptive Motion Estimation for Elastography Using Ultrasound Sequences," IEEE Transactions on Medical Imaging, vol. 24, No. 6, pp. 755-766 (2005).
Zheng, et al., "High Resolution ultrasound elastomicroscopy imaging of soft tissues: system development and feasibility; Ultrasound elastomicroscopy," Physics in Medicine and Biology, vol. 49, No. 17, pp. 3925-3938 (Sep. 7, 2004).
Chen et al., "Estimation of Displacement Vectors and Strain Tensors in Elastography Using Angular Insonifications." IEEE Transactions on Medical Imaging, vol. 23, No. 12, pp. 1479-1489 (Dec. 1, 2004).
Konofagou et al., "Elastographic Imaging of the Strain Distribution at the Anterior Cruciate Ligament and ACL-Bone Insertions" 27th Annual International Conference of the Engineering in Medicine and Biology Society, pp. 972-975 (Shanghai, China Sep. 1-4, 2005).
Qin et al., "The Natural Frequency of Nonlinear Oscillation of Ultrasound Contrast Agents in Microvessels," Ultrasound in Med. & Biol., vol. 33, No. 7, pp. 1140-1148, 2007.
Konofagou et al., "Noninvasive Electromechanical Wave Imaging and Conduction Velocity Estimation in Vivo," Ultrasonics Symposium, 2007 IEEE, pp. 969-972, 2007.
Konofagou et al., "Electromechanical Wave imaging for noninvasive mapping of the 3D electrical activation sequence in canines and humans in vivo,"Journal of Biomechanics, 45(5):856-864 (Mar. 15, 2012).
Otani et al., "Transmural ultrasound-based visualization of patterns of action potential wave propagation in cardiac tissue," Annals Biomedical Engineering, 38(10):3112-3123 (2010).
Chen et al., "Architectural Acoustics and Noise: Advancements and Best Practices in Instrumentation for Architectural Acoustics and Noise," J. Acoust. Soc. Am.; 164th Meeting: Acoustical Society of America, 132(3, Pt. 2):1977-2018 (Sep. 2012) Cited in IR Assessments: Chen, et al., Radiation-Force-Based Estimation of Acoustic Attenuation Using Harmonic Motion Imaging (HMI) in Phantoms and in Vito Livers Before and After HIFU Ablation, Ultrasound in Medicine and Biology, Submitted and included in IR Report.
Chen et al., "Engineering Acoustics and ASA Committee on Standards: Sound Intensity Measurements," J. Acoust. Soc. Am.; 164th Meeting: Acoustical Society of America, 132(3, Pt. 2):1984 (Sep. 2012); Cited in IR Assessment as: Chen, et al., Radiation-Force-Based Estimation of Acoustic Attenuation Using Harmonic Motion Imaging (HMI) in Phantoms and in Vito Livers Before and After HIFU Ablation, Ultrasound in Medicine and Biology, Submitted and included in IR Report.

Palmeri et al., "Characterizing Acoustic Attenuation of Homogeneous Media Using Focused Impulsive Acoustic Radiation Force," Ultrasonic Imaging, 28(2):114-128 (2006).
Duerinckx et al., "In vivo Acoustic Attenuation in Liver: Correlations with Blood Tests and Histology," Ultrasonic in Medicine & Biology, 14(5):405-413 (1988).
Fujii et al., "A New Method for Attenuation Coefficient Measurement in the Liver," Journal of Ultrasound in Medicine, 21(7):783-788 (2002).
Damianou et al., "Dependence of Ultrasonic Attenuation and absorption in dog soft tissues on Temperature and Thermal dose," The Journal of Acoustical Society of America, 102(1):628-634 (1997).
Techavipoo et al., "Temperature Dependence of Ultrasonic Propagation Speed and Attenuation in Excised Canine Liver Tissue Measured Using Transmitted and Reflected Pulses," The Journal of Acoustical Society of America, 115(6):2859-2865 (2004).
Papadakis, "Ultrasonic Instruments & Devices," Academic Press, 1999.
Cobbold, "Foundations of biomedical ultrasound," Biomedical engineering series, Oxford University Press, pp. 422-423(2006).
Jasaityte et al., "Current state of three dimensional myocardial strain estimation using echocardiography," Journal of the American Society of Echocardiography, 26(1):15-28 (2013).
Konofagou et al., "Noninvasive electromechanical wave imaging and conduction-relevant velocity estimation in vivo," Ultrasonics, 50(2):208-215 (2010).
Provost et al., "Imaging the electromechanical activity of the heart in vivo," Proceedings of the National Academy of Sciences, 108:8565-8570 (2011).
Provost et al., "Mapping of cardiac electrical activation with electromechanical wave imaging: An in silico-in vivo reciprocity study," Heart Rhythm, 8(5):752-759 (2011).
Otani et al., "Use of ultrasound imaging to map propagating action potential waves in the heart," Computers in Cardiology, 36:617-620 (2009).
Ginat et al., "High-resolution ultrasound elastography of articular cartilage in vitro," Proceedings of the 28th IEEE EMBS Annual International Conference, New York City, USApp. 6644-6647 (Aug. 30-Sep. 3, 2006).
Zheng et al., "Ultrasonic measurement of depth-dependent transient behaviors of articular cartilage under compression," Journal of Biomechanics, 38:1830-1837 (2005).
Shinna et al., "Realtime tissue elasticity imaging using the combined autocorrelation method," J. Med. Ultrasonics, 29(autumn):119-128 (2002).
Borden et al., "Ultrasound Radiation Force Modulates Ligand Availability on Target Contrast Agents," Mol. Imaging, 5:139-147 (2006).
Vial (en.wikipedia.org/wiki/Vial) downloaded May 20, 2014.
Luo et al., "Myocardial elastography at both high temporal and spatial resolution for the detection of infarcts," Ultrasound Med. Biol. 33(8): 1206-1223, 2007.
International Search Report for PCT/US2011/34704, dated Jun. 11, 2012.
Zwanenburg et al., (2004) "Timing of cardiac contraction in humans mapped by high-temporal-resolution MRI tagging: early onset and late peak of shortening in lateral wall," Am J Physiol Heart Circ Physiol 286:H1872-1880.
Walker et al., (1994) "A fundamental limit on the performance of correlation based phase correction and flow estimation techniques," Ultrasonics, Ferroelectrics and Frequency Control, IEEE Transactions on 41(5):644-654, Sep. 1994.
Pernot et al., "Electromechanical Imaging of the Myocardium at Normal and Pathological States", Ultrasonics Symposium, 2005 IEEE, pp. 1091-1094, 2005.
Fenster et al., "Three-dimensional ultrasound imaging," Physics in Medicine and Biology, 46(5):R67-R99 (2001).
De Craene et al., "Temporal diffeomorphic free-form deformation: Application to motion and strain estimation from 3D echocardiography," Medical Image Analysis, 16(2):427-450 (2012).

(56) References Cited

OTHER PUBLICATIONS

Housden et al., "Ultrasonic imaging of 3D displacement vectors using a simulated 2D array and beamsteering," Ultrasonics, 53(2):615-621 (2013).
DuBose et al., "Confusion and Direction in Diagnostic Doppler Sonography," Journal of Diagnostic Medical Sonography, 25(3):173-177 (2009).
Yuh, et. al., "Delivery of Systemic Chemotherapeutic Agent to Tumors by Using Focused Ultrasound: Study in a Murine Model," Radiology, 234(2): 431-437, 2005.
Tanter et al., "Ultrafast compound imaging for 2-D motion vector estimation: application to transient elastography," IEEE Trans Ultrason Ferroelectr Freq Control, vol. 49(10), pp. 1363-1374, 2002.
Brooks et al., "Electrical Imaging of the Heart," IEEE Signal Processing Magazine, vol. 14(1), pp. 24-42, Jan. 1997.
European Search Report dated May 6, 2014, in European Patent Application No. EP 10838238.
Allcock et al., "An ionically crosslinkable polyphosphazene: poly [bis (carboxylatophenoxy) phosphazene] and its hydrogels and membranes," Macromolecules, Jan. 1989, vol. 22(1), pp. 75-79.
Allcock et al., "Glyceryl polyphosphazenes: synthesis, properties, and hydrolysis," Macromolecules, Jul. 1988, vol. 21(7), pp. 1980-1985.
Allcock et al., "Hydrolysis pathways for aminophosphazenes," Inorganic Chemistry, Feb. 1982, vol. 21(2), pp. 515-521.
Allcock et al., "Synthesis of sugar-substituted cyclic and polymeric phosphazenes and their oxidation, reduction, and acetylation reactions," Macromolecules, Apr. 1983, vol. 16(4), pp. 715-719.
Bartlett, "Phosphorus assay in column chromatography," The Journal of Biological Chemistry, Mar. 1959, vol. 234(3), pp. 466-468.
Cortesi et al., "Sugar cross-linked gelatin for controlled release: microspheres and disks," Biomaterials, Sep. 1, 1998, vol. 19(18), pp. 1641-1649.
Epstein et al., "Preparation of alendronate liposomes for enhanced stability and bioactivity: in vitro and in vivo characterization," The AAPS Journal, Dec. 1, 2008, vol. 10(4), pp. 505-515.
Epstein-Barash et al., "Prolonged duration local anesthesia with minimal toxicity," Proceedings of the National Academy of Sciences of the United States of America, Apr. 28, 2009, vol. 106(17), pp. 7125-7130.
Feshitan et al., "Microbubble size isolation by differential centrifugation," Journal of Colloid and Interface Science, Jan. 15, 2009, vol. 329(2), pp. 316-324.
Grolleman et al., "Studies on a bioerodible drug carrier system based on polyphosphazene Part I. Synthesis," Journal of Controlled Release, Jan. 1, 1986, vol. 3(1-4), pp. 143-154.
Hern et al., "Incorporation of adhesion peptides into nonadhesive hydrogels useful for tissue resurfacing," Journal of Biomedical Materials Research Part A, Feb. 1, 1998, vol. 39(2), pp. 266-276.
Huang, "Liposomes in ultrasonic drug and gene delivery," Advanced Drug Delivery Reviews, Jun. 30, 2008, vol. 60(10), pp. 1167-1176.
Ito et al., "Dextran-based in situ cross-linked injectable hydrogels to prevent peritoneal adhesions," Biomaterials, Aug. 31, 2007, vol. 28(23), pp. 3418-3426.
Ito et al., "The prevention of peritoneal adhesions by in situ cross-linking hydrogels of hyaluronic acid and cellulose derivatives," Biomaterials, Feb. 2007, vol. 28(6), pp. 975-983.
Kheirolomoom et al., "Acoustically-active microbubbles conjugated to liposomes: characterization of a proposed drug delivery vehicle," Journal of Controlled Release, Apr. 23, 2007, vol. 118(3), pp. 275-284.
Leong et al., "Bioerodible polyanhydrides as drug-carrier matrices. I: Characterization, degradation, and release characteristics," Journal of Biomedical Materials Research Part A., Oct. 1, 1985, vol. 19(8), pp. 941-955.
Leong et al., "Bioerodible polyanhydrides as drug-carrier matrices. II. Biocompatibility and chemical reactivity," Journal of Biomedical Materials Research Part A, Jan. 1, 1986. vol. 20(1), pp. 51-64.
Liu et al., "Encapsulated ultrasound microbubbles: therapeutic application in drug/gene delivery," Journal of Controlled Release, Aug. 10, 2006, vol. 114(1), pp. 89-99.
Pitt et al., "Ultrasonic drug delivery—a general review," Expert Opinion on Drug Delivery, Nov. 1, 2004, vol. 1(1), pp. 37-56.
Rosen et al., "Bioerodible polyanhydrides for controlled drug delivery," Biomaterials, Apr. 1, 1983, vol. 4(2), pp. 131-133.
Sapra et al., "Ligand-targeted liposomes for cancer treatment," Current Drug Delivery, Oct. 1, 2005, vol. 2(4), pp. 369-381.
Schroeder et al., "Controlling liposomal drug release with low frequency ultrasound: mechanism and feasibility," Langmuir, Mar. 27, 2007, vol. 23(7), pp. 4019-4025.
Schroeder et al., "Ultrasound, liposomes, and drug delivery: principles for using ultrasound to control the release of drugs from liposomes," Chemistry and Physics of Lipids, Nov. 30, 2009, vol. 162(1), pp. 1-16.
Szoka Jr. et al., "Comparative properties and methods of preparation of lipid vesicles (liposomes)," Annual Review of Biophysics and Bioengineering, Jun. 1980, vol. 9(1), pp. 467-508.
Tsutsui et al., "The use of microbubbles to target drug delivery," Cardiovascular Ultrasound, Nov. 16, 2004, vol. 2(1), p. 23.

* cited by examiner

US 10,010,709 B2

COMPOSITION FOR ON-DEMAND ULTRASOUND-TRIGGERED DRUG DELIVERY

CROSS-REFERENCE TO RELATED APPLICATIONS

This application is a U.S. national stage application of International Application No. PCT/US2010/060691, filed on Dec. 16, 2010, which claims priority to and the benefit of U.S. Provisional Application No. 61/287,159 filed on Dec. 16, 2009, the content of which is incorporated herein by reference in its entirety.

FIELD OF THE INVENTION

The present invention is in the field of drug delivery, particularly on-demand drug delivery triggered by ultrasound.

BACKGROUND OF THE INVENTION

On-demand drug delivery systems allow a patient or a medical practitioner to modulate the location, timing and extent of drug release. Many different approaches have been used in drug delivery systems to create on-demand drug release. In some systems, triggers such as near-infrared light, magnetically induced heating, and ultrasound are used to control drug release. Similarly, a variety of formulations have been employed ranging from nanoparticulate to macroscopic formulations.

The principal limitations of many prior approaches have been that the particulate ones frequently result in a single drug release event, while more macroscopic devices that can release multiple doses often require surgical implantation and/or contact with external electrical or other equipment.

Therefore there is a need for improved drug delivery systems that are capable of modulation by a patient or medical practitioner.

It is an object of the invention to provide a drug delivery system for which the drug release can be modulated by a patient and/or a medical practitioner.

It is a further object of the invention to provide a method for modulating drug release in a drug delivery system.

SUMMARY OF THE INVENTION

Injectable or implantable drug delivery systems providing on-demand ultrasound-triggered drug release and methods for controlling the release of drug in a patient are provided herein. The on-demand drug delivery systems contain a drug depot and a drug encapsulated in an encapsulating material, where the encapsulating material is different from the depot. In the preferred embodiment, the depot also contains microbubbles that encapsulate one or more gases. The microbubbles enhance the drug release when ultrasound is applied compared to the same system in the absence of microbubbles.

In a particularly preferred embodiment, the drug delivery system is an injectable, multi-component system for providing on-demand, ultrasound-triggered drug release, containing an encapsulating material, preferably liposomes, microbubbles and a hydrogel. In use, the liposomes carry the drugs and prevent their premature release. The microbubbles enhance the drug release compared to the same system in the absence of the microbubbles, and the hydrogel maintains both the encapsulating materials and the microbubbles in close proximity to each other and in a relatively constrained location so that they can affect release when ultrasound is applied.

This system can accommodate a broad range of total drug payload and patterns of drug release, depending on the parameters of drug loading, encapsulating material concentration, microbubble loading, pulse time, and pulse intensity. Generally ultrasound will be administered at a suitable frequency and intensity for a suitable period of time to release the desired dosage from the drug depot without causing tissue injury. In a preferred embodiment, ultrasound is applied as a short pulse at relatively low intensity (e.g., 1-min pulsed cycles, 10-sec on, 1-sec off). Additionally, the ultrasound can be administered for a suitable period of time and/or at a suitable intensity for precise determination of the magnitude of the drug dose to be delivered, by modulating either the intensity or the duration of the ultrasound pulse.

BRIEF DESCRIPTION OF THE DRAWINGS

FIG. 4A shows the results for mesothelial cells (CRL-9444 cell line).

DETAILED DESCRIPTION OF THE INVENTION

Figure 1:
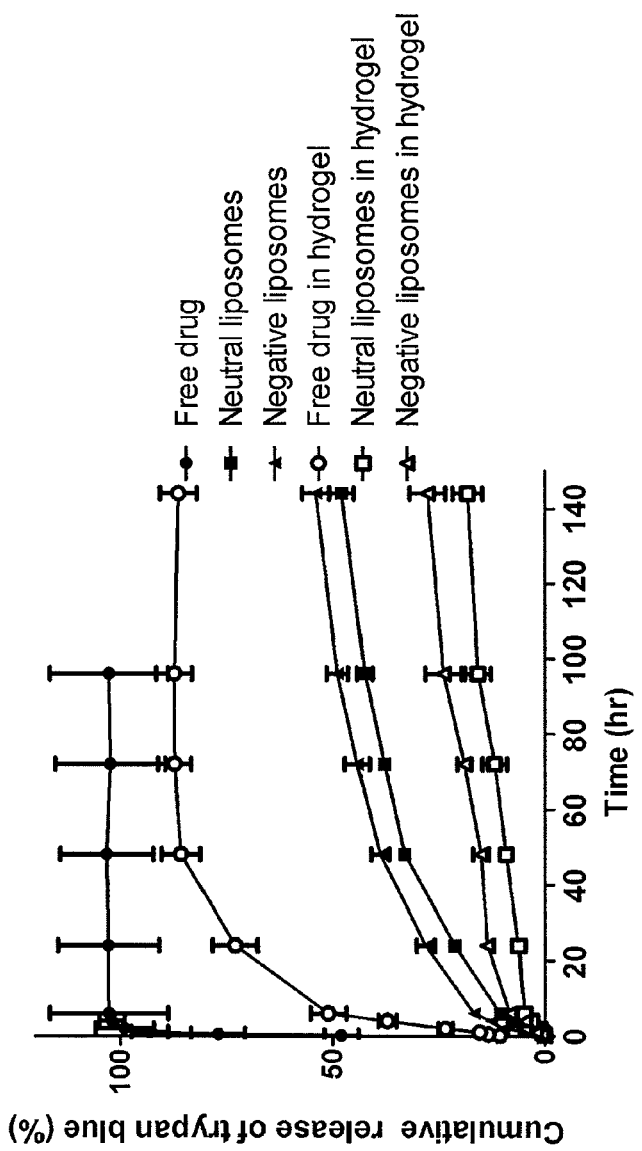
FIG. 1 is a graph of the cumulative in vitro release (%) of trypan blue from dextran-CHO/CMC-ADH hydrogels, either free in the gel matrix or encapsulated in negatively charged and neutral lipid-based liposomes in PBS at 37° C., over time (hours). Data are means with standard deviations (n=4).

Injectable or implantable drug delivery systems providing on-demand ultrasound-triggered drug release and methods for controlling the release of drug in a patient are provided herein. In the preferred embodiment, the release of drug can be controlled for longer than one day, preferably longer than one week, preferably for at least 14 days, more preferably for up to one month following injection or implantation of the depot in a patient. In some embodiments, the release of drug can be controlled for up to one year following injection or implantation in a patient.

The amount of drug released is controlled by the frequency, intensity and duration of the ultrasound that is administered. Once the ultrasound is turned off, the depot formulation stops releasing drug. It resumes releasing drug following another application of ultrasound.

In a preferred embodiment, the depot is a hydrogel. However, other materials, including polymers that form non-hydrogel matrices following crosslinking, may be used. The depot contains one or more drugs or biologics to be delivered encapsulated in an encapsulating material. In a preferred embodiment the drug is encapsulated in liposomes. However, other encapsulating materials, such as nanoparticles, microparticles, or particles greater than 500 microns in size may be used. In a particularly preferred embodiment, the depot also contains microbubbles. The microbubbles may contain any biocompatible gas or mixture of gases. The microparticles enhance drug release from the encapsulating material in response to ultrasound by increasing the difference between baseline and peak release rates compared to the release from the same drug depot in the absence of the microparticles.

Following injection or implantation of the hydrogel, the patient or a medical practitioner applies ultrasound, preferably low frequency ultrasound, as needed, to regulate the delivery of the encapsulated drug.

I. On-Demand Drug Delivery Systems

The on-demand drug delivery systems contain a drug depot and a drug encapsulated in an encapsulating material, where the encapsulating material is different from the depot. In the preferred embodiment, the depot also contains microbubbles that encapsulate one or more gases. The microbubbles enhance the drug release when ultrasound is applied compared to the same system in the absence of microbubbles.

A. Drug Depot

The drug depot entraps the encapsulating material and the drug encapsulated therein and controllably and repeatedly releases the drug following the application of ultrasound. Typically the drug depot is a polymeric material that degrades in the presence of an ultrasound beam. Drug release may occur due to polymer degradation following the administration of ultrasound. After the ultrasound is turned off or transducer is removed from the patient, the depot continues to entrap the remaining encapsulating material and drug, subject to any release due to polymeric degradation that typically occurs in vivo, until the next application of ultrasound.

In one embodiment the drug depot contains a ligand that directs the attachment of the drug depot to the desired site in the patient. In another embodiment, the drug depot is bioadhesive or mucoadhesive.

The depot may be formed by crosslinking injectable precursor components to form a crosslinked matrix that serves as the drug depot. "Precursor components" as generally used herein means the monomers, oligomers and/or polymers suitable for forming the drug depot.

"Crosslinking" as generally used herein means the formation of more than one covalent linkage within or between molecules. In another embodiment, the depot is preformed and is an implantable material.

Preferably the depot is a gel, more preferably the depot is a hydrogel. "Gel" refers to a colloid in which the disperse phase has combined with the dispersion medium to produce a semisolid material. Gels are substantially dilute crosslinked systems, which exhibit no flow when in the steady-state. By weight, gels are mostly liquid, yet they behave like solids due to a three-dimensional crosslinked network within the liquid. It is the crosslinks within the fluid that give a gel its structure (hardness) and contribute to stickiness (tack).

"Hydrogel" refers to a class of polymeric materials which are swollen in an aqueous medium, but which do not dissolve in water. Hydrogels are highly absorbent (they can contain over 99% water) natural or synthetic polymers. Hydrogels also possess a degree of flexibility very similar to natural tissue, due to their significant water content.

In one embodiment the drug depot may be formed from precursor components to form a porous polymeric matrix that serves as the drug depot.

1. Injectable Precursors

The precursor components can be monomeric, oligomeric or polymeric. Any precursor components that form a biocompatible gel upon crosslinking, and preferably form a hydrogel, may be used.

a. Hydrogel Forming Precursors

A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide (PEO)-polypropylene glycol (PPG) block copolymers which are crosslinked by temperature or pH, respectively.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix.

Polyphosphazenes are polymers with backbones consisting of nitrogen and phosphorous separated by alternating single and double bonds. Each phosphorous atom is covalently bonded to two side chains.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazene (PCPP) can be synthesized, which is cross-linked with dissolved multivalent cations in aqueous media at room temperature or below to form a hydrogel.

Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. The term bioerodible or biodegradable, as used herein, means a polymer that dissolves or degrades within a period that is acceptable in the desired application, less than about five years and most preferably less than about one year, once exposed to a physiological solution of pH 6-8 having a temperature of between about 25° C. and 37° C. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups.

Methods for synthesis and the analysis of various types of polyphosphazenes are described by Allcock, et al., Macromolecules 16, 715 (1983); Allcock, et al., Macromolecules 21, 1980 (1988); Allcock, et al., Inorg. Chem. 21(2), 515-521 (1982); Allcock, et al., Macromolecules 22, 75 (1989); U.S. Pat. Nos. 4,440,921, 4,495,174 and 4,880,622 to Allcock, et al.; U.S. Pat. No. 4,946,938 to Magill, et al.; and Grolleman, et al., J. Controlled Release 3, 143 (1986).

Methods for the synthesis of the other polymers described above are known to those skilled in the art. See, e.g., Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available.

In one embodiment, a water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations, such as alkylammonium salts, can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer. Higher concentrations are limited by the solubility of the salt.

Anions for cross-linking of the polymers to form a hydrogel are generally divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, having a preferred molecular weight between 3,000 and 100,000 Da, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

In one embodiment the hydrogel is a natural hydrogel material, such as agarose, methylcellulose, hyaluronan, and other naturally derived polymers.

In one embodiment, the hydrogels is formed by cross-link in situ via the formation of hydrazone bonds. Suitable precursor components include: dextran, hyaluronic acid (HA); carboxymethylcellulose (CMC); optionally with aldehyde modification, (—CHO) or adipic hydrazide modification, (-ADH).

In another embodiment, the hydrogel is a silicone hydrogel. In one embodiment, the hydrogel is formed from injectable precursor components such as polyacrylamides, crosslinkable PEO, PVP, or PolyAMPS, or poly(2-acrylamido-2-methyl-1-propanesulfonic acid), PEO-PPO block copolymers, polyvinyl alcohol, sodium polyacrylate, acrylate polymers and copolymers with an abundance of hydrophilic groups.

In one embodiment the gel is an organogel. The organogel may be a lecithin-based organogel. The organogel may be formed from glyceryl fatty acid esters, a non-ionic surfactant, such as sorbitan monostearate, and/or poly(acrylic acid) (PAA).

Suitable precursor components for forming the drug depot include proteins, peptides, polyoxyalkylenes, poly(vinyl alcohol), poly(ethylene-co-vinyl alcohol), poly(acrylic acid), poly(ethylene-co-acrylic acid), poly(ethyloxazoline), poly(vinyl pyrrolidone), poly(ethylene-co-vinyl pyrrolidone), poly(maleic acid), poly(ethylene-co-maleic acid), poly(acrylamide), poly(ethylene oxide)-co-poly(propylene oxide) block copolymers or poly hydroxyl acids, such as polylactic acid and polyglycolic acid and copolymers thereof. Optionally one of the precursor components is a synthetic peptide.

Functionalized PEG has properties of high hydrophilicity and low degradability by mammalian enzymes and low toxicity, which make PEG particularly useful for application in the body. One can readily purchase or synthesize linear (meaning with two ends) or branched (meaning more than two ends) PEGs and then functionalize the PEG end groups according to the reaction mechanisms of choice.

Drug depots for application to a patient can be prepared in a variety of ways. Some depots are prepared through free-radical polymerization between two or more precursor components containing unsaturated double bonds, such as described in Hern, et al., J. Biomed. Mater. Res. 39:266-276, 1998. Other depots are prepared by reacting a first precursor component containing two or more nucleophilic groups, X, with at least a second precursor component containing two or more electrophilic groups, Y, which are capable of cross-linking with the nucleophilic group on the first precursor component. The reaction mechanism involved can be a nucleophilic substitution reaction, such as disclosed in U.S. Pat. No. 5,874,500, a condensation reaction and/or a Michael type addition reaction, such as described in WO 00/044808. Suitable nucleophilic groups, X, include: —$NH_2$, —SH, —OH, —$PH_2$, and —CO—NH—$NH_2$. Suitable electrophilic groups, Y, include: —$CO_2N(COCH_2)_2$, —$CO_2H$, CHO, —$CHOH_2$, —N=C=O, —$SO_2CH$=$CH_2$, —N(COCH), and —S—S—($C_5H_4N$). A precursor component may have one or more nucleophilic groups, where the nucleophilic groups may be the same or different from each other. The second precursor component may have one or more electrophilic groups, where the electrophilic groups may be the same or different from each other. Thus a precursor component may have two or more different functional groups.

The 1,4 addition reaction of a nucleophilic group on a conjugate unsaturated system is referred to as a Michael type addition reaction. A Michael type addition reaction allows for in situ cross-linking at the site of need in the body of at least a first and a second precursor component under physiological conditions in a self-selective manner, even in the presence of sensitive biological materials. Thus the first precursor component reacts much faster with a second precursor component than with other components in the sensitive biological environment, and the second precursor component reacts much faster with the first precursor component than with other components in the sensitive biological environment present in the body. When one of the precursor components has a functionality of at least two, and at least one of the other precursor components has a functionality of greater than two, the system will self-selectively react to form a cross-linked three dimensional biomaterial.

2. Injectable/Implantable Solid Implants as Drug Depot

Polymeric implants may be used as the drug depot. In one embodiment, precursor is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the encapsulated drug and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compositions can be incorporated into a polymer matrix and molded or compressed into a device that is a solid at room temperature. For example, the compositions can be incorporated into a biodegradable polymer, such as polyanhydrides and copolymers thereof, polyhydroalkanoic acids and copolymers thereof, PLA, PGA, and PLGA, and compressed into solid device, such as disks, or extruded into a device, such as rods.

In one embodiment, the drug depot is a polymeric matrix that is sufficiently hydrophobic so that it retains its integrity for a suitable period of time when placed in an aqueous environment, such as the body, and stable enough to be stored for an extended period before use. The polymeric matrix should provide a suitable degradation profile, so that it remains in the patient's body for a suitable period of time to release the drug, while degrading into biocompatible degradation products. The polymeric matrix should be sufficiently strong and flexible so that it does not crumble or fragment during use.

Biocompatible polymers can be categorized as biodegradable and non-biodegradable. Biodegradable polymers degrade in vivo as a function of chemical composition, method of manufacture, and implant structure. Synthetic and natural polymers can be used although synthetic polymers are preferred due to more uniform and reproducible degradation and other physical properties. Examples of synthetic polymers include polyanhydrides, polyhydroxyacids such as polylactic acid, polyglycolic acids and copolymers thereof, polyesters, polyamides, polyorthoesters, and some polyphosphazenes. Examples of naturally occurring polymers include proteins and polysaccharides such as collagen, hyaluronic acid, albumin and gelatin. Drug can be encapsulated within, throughout, and/or on the surface of the implant.

There are two general classes of biodegradable polymers: those degrading by bulk erosion and those degrading by surface erosion. An aromatic monomer such as p-carboxyphenoxy propane (CPP) may be copolymerized with a monomer such as sebacic acid (SA) to form a copolymer, such as CPP-SA (20:80).

Use of polyanhydrides in controlled delivery devices has been reported by Leong, et al., J. Med. Biomed. Mater. Res. 19, 941 (1985); J. Med. Biomed. Mater. Res. 20, 51 (1986); and Rosen, et al., Biomaterials 4, 131 (1983). The release and physical properties required for processing into implants are largely determined by the hydrophobicity and molecular weight, with higher molecular weight polymers having more desirable physical properties. Aromatic polyanhydrides exhibit near zero order (linear) erosion and release kinetics, but have very slow degradation rates. For example, it was estimated that it would take a delivery device prepared from p-CPP more than three years to completely degrade in vivo. Polymers prepared from linear aliphatic diacids are hydrophilic solids that degrade by bulk erosion, resulting in a rapid release of the drug from the polymeric matrix. Further, anhydride homopolymers based on aromatic or linear aliphatic dicarboxylic acids are highly crystalline and have poor film forming properties. Aromatic polyanhydrides also have high melting points and low solubility in organic solvents. Copolymerizing the linear aliphatic diacids with aromatic diacids, to form, for example, the copolymer of poly 1,3-(bis(p-carbophenoxy)propane anhydride (p-CPP) (an aromatic polyanhydride) with sebacic acid (a copolymer of an aromatic diacid and an aliphatic diacid), can be used to obtain polymers having appropriate degradation times. As described in U.S. Pat. No. 4,757,128 to Domb and Langer, high molecular weight copolymers of aliphatic dicarboxylic acids with aromatic diacids are less crystalline than aromatic or linear aliphatic polyanhydrides, and they form flexible films. U.S. patents that describe the use of polyanhydrides for controlled delivery of substances include U.S. Pat. No. 4,857,311 to Domb and Langer, U.S. Pat. No. 4,888,176 to Langer, et al., and U.S. Pat. No. 4,789,724 to Domb and Langer.

Other polymers such as polylactic acid, polyglycolic acid, and copolymers thereof have been commercially available as suture materials for a number of years and can be readily formed into devices for drug delivery.

Non-biodegradable polymers remain intact in vivo for extended periods of time (years). Drug loaded into the non-biodegradable polymer matrix is released by diffusing through the polymer's micropore lattice, which can be tailored to provide a rapid or a slower release rate by altering the percent drug loading, porosity of the matrix, and implant structure. Ethylene-vinyl acetate copolymer (EVAc) is an example of a nonbiodegradable polymer that has been used as a local delivery system. Others include polyurethanes, polyacrylonitriles, and some polyphosphazenes.

B. Encapsulating Materials

The drug is encapsulated in an encapsulating material, such as a liposome, microparticle, nanoparticle, or particle with a diameter greater than 500 microns. Preferably the drug is encapsulated in a liposome. The drug encapsulating material is selected so that the baseline rate of drug release is minimal. This allows the system to release drug on-demand for a sustained period of time, preferably for at least 14 days following administration to the patient.

1. Liposomes

Liposomes are lipid vesicles composed of concentric phospholipid bilayers which enclose an aqueous interior. The lipid vesicles comprise either one or several aqueous compartments delineated by either one (unilamellar) or several (multilamellar) phospholipid bilayers. Sapra, et al., Curr Drug Deliv 2, 369-81 (2005).

The overall charge for the liposome may be neutral, positive or negative. Preferably the overall charge for the liposome is neutral or the same as the charge of the drug to be encapsulated, if the drug has an overall charge.

Liposomes are microscopic or submicroscopic structures typically having a diameter in the range of 10 nm to 20 □m. Liposomes are made up of one or many concentrically arranged lipid bilayers constituting an envelope. The basic components of liposomes are amphiphilic compounds having clearly separated hydrophilic and hydrophobic centers. Hydrophilic components of lipids in the bilayer are directed towards aqueous phases (external and internal), whereas the hydrophobic components of both lipid layers are directed towards one another, forming the internal layer of a membrane. The compounds most often used for the preparation of liposomes preparation are phospholipids; however, liposomes have also been prepared from single-chain natural or synthetic amphiphiles, such as lipid acids, saponins and/or detergents. Liposomes can also be prepared by derivatizing phospholipids with a biocompatible, hydrophilic polymer as described in U.S. Pat. No. 6,930,087 to Baru et al.

Liposomes can be used to encapsulate hydrophilic, hydrophobic and amphiphilic materials. Hydrophilic materials are encapsulated in the internal aqueous phase while hydrophobic materials are incorporated into the lipid bilayer and amphiphilic materials are absorbed onto the double lipid membrane. Moreover, charged active substances may be attached to the surface of the bilayer. One can influence the degree of active agent incorporation and/or the release profile of the active agent by modifying the bilayer composition as well as the size and layer structure of the liposomes.

2. Nanoparticles and Microparticles

Solid nanoparticles and microparticles differ from liposomes and niosomes in that they are prepared from polymers and do not have an aqueous core but a solid polymer matrix, often the polymeric matrix has pores throughout the matrix and/or on the surface of the matrix. Microparticles and nanoparticles may be prepared by the controlled precipitation of polymers solubilised in one of the phases of an emulsion. Precipitation of the polymer out of the solvent takes place on solvent evaporation, leaving particles of the polymer suspended in the residual solvent. Drug loading in both instances occurs simultaneously with particle formation and the presence of surfactants in the aqueous phase may be used to ensure a small particle size.

Microparticles may also be prepared by chemical cross-linking of soluble polymers and nanoparticles by the polymerisation of a monomer in a good solvent for the monomer but a poor solvent for the polymer or by high-pressure homogenis-ation. The loading of water soluble drugs into the hydrophobic polymer particle matrix is still difficult but may be enhanced by the salting out of the active ingredient with soluble inorganic salts, the formation of lipophilic ion pairs of soluble amine drugs with monalkyl phosphate esters, or by exploiting the ionic attraction between basic amine drugs and the carboxylic groups of polylactic acid co-glycolic acid.

The polymers may be biodegradable, non-biodegradable, or bioerodible. Suitable polymers include, but are not limited to, polystyrene, polylactic acid, polyglycolic acid, poly-hydroxyalkanoates, such as poly β-hydroxybutyrate, fibrin, and alkyl cyanoacrylates. These solid nanoparticles and microparticles may be used to prepare sustained release parenteral formulations or to achieve drug targeting. Nanoparticles are generally defined as particulate dispersions having a particle size of between 30 and 500 nm while microparticles are generally defined as particulates having a particle size greater than 0.5 microns and less than or equal to 100 microns.

Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the body by means including enzymatic degradation and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to, hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et al., (Phila, Lippencott, Williams & Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

C. Microbubbles

The microbubbles contain a gas core surrounded by an envelope formed from one or more lipids and one or more emulsifying agents in the form of a lipid monolayer or multilayer. The outer surface of the envelope forms a protective film.

1. Envelope

The envelope is in the form of a lipid film, in the form of a monolayer or multilayer, preferably in the form of a monolayer. The lipid film may be between 1 and 100 nm thick, preferably between 1 and 10 nm thick, most preferably between 2 and 5 nm thick. In one preferred embodiment, the lipid film is a monolayer that is about 10 nm thick.

The overall charge for the lipid envelope may be neutral, positive or negative.

The envelope may contain one or more emulsifying agents. The emulsifying agent generally contains a hydrophilic portion, typically a hydrophilic polymer, and a hydrophobic portion. The emulsifying agent or a portion thereof, generally the hydrophilic portion of the emulsifying agent, forms a protective border on the outer surface of the microbubble. Preferably the border is in the form of a brush where the hydrophilic portion of the emulsifying agent extends from the lipid containing portion of the envelope to form a border on the outer surface of the microbubble.

a. Lipids

A variety of lipids may be used to form the lipid film. The lipids may be natural or synthetic. Suitable lipids include phospholipids, fatty acids, triacyl glycerols, sphingolipids, terpenes, and waxes. Preferably the envelope contains one or more phospholipids.

The lipid envelope may contain lipids with acyl chains of varying lengths and degrees of saturation. The lipid envelope may contain lipids with a single acyl chain length, or different lipids with different acyl chain lengths. In a preferred embodiment, the lipid is a long-chain lipid, preferably a saturated diacyl phosphatidylcholine (Di-$C_n$—PC, where n is between 12 and 24, preferably where n is 16 or 18). Suitable lipids include phosphocholines, phosphoglycerols, phosphatidic acids, phosphoethanolamines, and phosphoserines. Examples include 1,2-Dilauroyl-sn-Glycero-3-Phosphocholine (dilauroylphosphatidylcholine, DLPC), 1,2-Dimyristoyl-sn-Glycero-3-Phosphocholine (dimyristoylphosphatidylcholine, DMPC), 1,2-Dipentadecanoyl-sn-Glycero-3-Phosphocholine (dipentadecanoyl-phosphatidylcholine, DPDPC), 1,2-dipalmitoyl-sn-Glycero-3-Phosphocholine (dipalmitoylphosphatidylcholine, DPPC), 1-Myristoyl-2-Palmitoyl-sn-Glycero-3-Phosphocholine (1-myristoyl-2-palmitoylphosphatidylcholine, MPPC), 1,2-Dimyristoyl-sn-Glycero-3-[Phospho-rac-(1-glycerol)] (DMPG), 1,2-Dimyristoyl-3-Trimethylammonium-Propane, cholesterol and its derivatives, fatty acids, fatty alcohols, and fatty esters.

i. Acyl Chain Length

Lipids in the envelope may have different acyl chain lengths. The number of carbons in the acyl chains of the lipids may range from 10 to 24 carbons. The average acyl chain length of the lipids in microbubbles typically ranges from 10 to 24 carbons. For example, the average acyl chain length of the lipids may be 20, 18, 16, 14, 13, or 12 carbons. The envelope may include one or more synthetic lipids with asymmetric acyl chains, where one acyl chain is longer than another.

Lipids with longer acyl chain lengths are generally preferred compared to lipids with shorter chain lengths. Generally lipids with longer chain lengths produce more microbubbles with a greater shelf life. However, the chain length should not be too long.

Generally, longer chained lipids (e.g. 24-carbon vs. 16-carbon) are more resistant to oxygen passage. Resistance to gas release is also increased in walls composed of saturated (i.e. no double bonds) versus unsaturated lipids. Lipids with one or more double bonds contain kinks in the acyl chains due to the presence of the double bonds, which creates irregularities in the packing geometry, and thereby allows for gas to transfer out of the microbubble more rapidly.

A lipid film comprising lipids having longer chain lengths may have decreased permeability to gases compared to one with lipids with shorter acyl chain lengths. This decreased permeability may be attributed to an increase in attractive dispersion and hydrophobic forces between the hydrophobic tails of adjacent lipid molecules, resulting in a more cohesive lipid film. However, longer acyl chains generally provide greater envelope cohesion, which can improve mechanical strength and reduced gas escape kinetics.

In some applications for the microbubbles may contain short acyl chain lengths (e.g. ≤C14). Shorter acyl chain lengths are generally more unstable than longer acyl chains.

ii. Phase Transition Temperature

As used herein, the "phase transition temperature" ($T_m$) refers to the temperature at which lipid assemblies transition from a solid (crystalline) phase to a fluid (liquid crystalline) phase. For example, 1,2-Dipentadecanolyl-sn-Glycero-3-Phosphocholine (C15) has a $T_m$ of 33° C. Thus this lipid is in the solid phase at room temperature and transitions to the fluid phase when it is injected into the body.

Lipids in the fluid phase exhibit significantly higher thermal motion, creating higher gas permeability and a significantly higher surface tension compared to the same lipids in the solid phase. Lipids in solid phase are tightly packed together with minimal lipid motion, making them less permeable to gas transfer. A microbubble containing lipids that are in the fluid phase generally has increased surface tension and gas permeability compared to the same microbubble containing the same lipids in the solid phase.

Shell cohesion, as a function of acyl chain length, may be represented by the reduced temperature ($T_R$), which is equal to the ratio of the ambient temperature (or "working temperature") (T) to the main phase transition temperature ($T_m$) of the lipid (in Kelvin). For $T_R>1$, the shell is in an expanded (fluid) state at the working temperature. For $T_R<1$, the shell is in a condensed (solid) state at the working temperature. See Table 2 for a list of lipids with their corresponding main phase transition temperatures ($T_m$) and reduced temperatures ($T_R$).

b. Emulsifying Agent

"Emulsifying agent(s)" refers to the one or more surfactants in the envelope that contain a molecule aiding lipid adsorption to the gas/liquid interface and stabilizing the microbubble to prevent coalescence. Typically, the surfactant is a hydrophilic polymer attached to a hydrophobic anchor via one or more covalent bonds. Preferably the hydrophobic anchor is a lipid. The hydrophobic anchor may be an alkyl group, in the form of a single chain or multiple chains. Typically the alkyl group is 12 to 24 carbons in length. Alternatively, hydrophobic anchors such as sterols, or polymers such as polycaprolactone may be used.

Preferably the hydrophilic polymer in the emulsifying agent is polyethylene glycol (PEG). Typical weight average molecular weights for PEG range from about 550 Da to 5,000 Da. Alternatively, other molecules can be in place of PEG. Alternatives include polypropylene glycol, polyvinyl alcohol, poly-N-vinyl pyrrolidone and copolymers thereof, mixed polyalkylene oxides having a solubility of at least one gram/liter in aqueous solutions such as some poloxamer nonionic surfactants, neutral water-soluble polysaccharides, including dextran, Ficoll, and derivatized celluloses, non-cationic poly(meth)acrylates, non-cationic polyacrylates, such as poly(meth)acrylic acid, and esters amide and hydroxyalkyl amides thereof, and combinations thereof.

The envelope may contain a variety of different amounts of base lipids and emulsifying agents. An optimum ratio of emulsifying agents to base lipids, which lies between a minimum ratio needed to have sufficient amounts of emulsifying agents to aid in lipid adsorption, shield the surface of the microbubble and prevent coalescence and a maximum ratio where lateral repulsion forces due to the presence of the emulsifying agent begin to significantly disrupt packing of the base lipid, may be determined experimentally.

i. PEGylated Lipids

Emulsifying agents formed of a lipid and PEG are referred to herein as "PEGylated lipids". The PEgylated lipid may contain the same lipid as the base lipid in the envelope. Alternatively, the PEGylated lipid may contain a lipid that is different from the base lipid in the envelope. Examples of suitable PEGylated lipids include 1,2-Distearoyl-sn-glycero-3-Phosphoethanolamine-N-[Methoxy (Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000].

2. Optional Molecules

In one embodiment, one or more proteins or polymers may be used in place of the one or more lipids to stabilize the microbubble.

Optionally, the envelope may include one or more molecules in addition to the lipid(s) and emulsifying agent(s) to stabilize the microbubbles. Suitable stabilizers include polymers and proteins. Suitable polymers include lipophilic and amphiphilic polymers. The proteins and polymers may be within the lipid monolayer or multilayer.

The proteins may be a single protein or a mixture of proteins. Suitable proteins include lipophilic and amphiphilic proteins. Exemplary proteins include lung surfactant proteins, such as SP-A, SP-B, SP-C, or SP-D, synthetic lung surfactant proteins, lung surfactant protein mimetics, and derivatives thereof.

Alternatively the protein may be in a coating on the surface of the envelope.

3. Gas Core

The gas core contains at least one gas or gas precursor. The gas must be pharmacologically acceptable, i.e. biocompatible and have minimal toxicity when released. The gas precursor is a material that forms a gas following administration of the microbubbles to the patient. Suitable gas precursors include volatile liquids.

The gas may be a fluorinated gas, such as fluorinated gases include $CF_4$, $C_2F_4$, $C_2F_6$, $C_3F_6$, $C_3F_8$, $C_4F_8$, $C_4F_{10}$, and $SF_6$. The gas may be a perfluorocarbon that is a gas at body temperature, such as $CF_4$, $C_2F_4$, $C_2F_6$, $C_3F_6$, $C_3F_8$, $C_4F_8$, and $C_4F_{10}$. n-Perfluorobutane ($C_4F_{10}$) is an insoluble gas that will not condense at the temperature of use and is pharmacologically acceptable. Other suitable gases include carbon dioxide, nitrogen, nitrous oxide, helium, argon, nitric oxide, xenon, carbon monoxide, nitric oxide, and volatile anesthetics, such as isoflurane. These gases may be in the gas core alone or in combination with one or more other gases.

The amount of gas contained with the microparticles will depend on the type of gas.

D. Drugs to be Delivered

One or more drugs, i.e. pharmaceutically active agents, are encapsulated in the encapsulating material. Suitable classes of active agents include, but are not limited to, antibiotic agents, antimicrobial agents, anti-acne agents, antibacterial agents, antifungal agents, antiviral agents, steroidal anti-inflammatory agents, non-steroidal anti-inflammatory agents, anesthetic agents, antipruriginous agents, antiprotozoal agents, anti-oxidants, antihistamines, vitamins, and hormones.

In place of the drug, or in addition to the drug, another active agent, such as a biologic, such as a cellular material, DNA, RNA, siRNA, vaccines, blood or blood components, allergenics, somatic cells, gene therapy, tissues, and recombinant therapeutic proteins created by biological processes, growth factors, hormones, or proteins or peptides may be encapsulated in the encapsulating material.

A variety of different pharmaceutically active agents can be incorporated into the encapsulating material. In general, drugs or other active agent are included in the encapsulating material in a range of from 1% to 99% (w/w) based on the weight of the encapsulating material, such as between 10 and 50% (w/w), although the optimum can vary widely depending on the drug, disease or disorder to be treated, and encapsulating material.

Once injected or implanted in a patient, the drug delivery system may be used for applications where high local concentrations of drug are desired, such as local anesthesia or chemotherapy. In another embodiment, the drug delivery system is designed to systemically deliver a drug, such as a narcotic.

1. Analgesics and Local Anesthetics

Products for the moderation of pain, referred to as analgesics, represent one of the largest markets targeted by pharmaceutical companies. In one embodiment, the drug delivery system delivers one or more analgesics.

Pharmaceutical analgesics include a variety of classes of drugs, such as general anesthetics, non-steroidal anti-inflammatories, and local anesthetics. General anesthetics reduce pain by producing a loss of consciousness. Local anesthetics cause a loss of sensation in a localized area of the body without a loss of consciousness. Non-steroidal anti-inflammatories may ameliorate the pain but do not cause a loss of sensation or consciousness. Among the general anesthetics are centrally acting narcotics, including morphine, demerol, fentanyl and codeine. These drugs act through opiate receptors in the central nervous system. Non-steroidal anti-inflammatory drugs (NSAIDs) include ibuprofen, indomethacin, acetaminophen, piroxicam, naproxen, flufenamic acid and mefenamic acid.

a. Local Anesthetics

In one embodiment, the drug is a local anesthetic and the drug delivery system is used to administer anesthesia to a patient. Local anesthetics block the generation and conduction of nerve impulses by increasing the threshold for electrical excitation in the appropriate nerve, by slowing the propagation of the nerve impulse, and by reducing the rate of rise of the action potential. Local anesthetics are extremely potent and result in a virtually complete loss of sensation in the treated area of the body.

As used herein, local anesthetic (LA) refers to any agent that produces nerve blockade within a specific area, region or site. Suitable local anesthetics include site 1 sodium channel blockers, lidocaine or lidocaine derivatives bupivacaine, mepivacaine, tetracaine, and ropivacaine. Other suitable charged local anesthetics include, but are not limited to, charged tetracaine derivatives (e.g., N-butyl tetracaine) and permanently charged derivatives of flecainide.

Additional anesthetics include, but are not limited to, chlorprocaine, dibucaine, etidocaine, dyclonine, hexylcaine, procaine, cocaine, ketamine, pramoxine and phenol.

b. Non-Steroidal Anti-Inflammatory Agents

Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

c. Steroidal Anti-Inflammatory Agents

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

2. Chemotherapeutics

Alternatively, the drug may be a chemotherapeutic. This is particularly useful for locally delivering the chemotherapeutic drug to the site of a cancer tumor, thereby avoiding systemic administration of the chemotherapeutic. This system allows for the delivery of a lower dosage than the dosage administered systemically to achieve the same effect.

The chemotherapeutic agent may be chemotherapeutic drugs an alkylating agent, antimetabolite, anthracycline, plant alkalois, topoisomerase inhibitor, or other antitumour agents. Alternatively the chemotherapeutic may be a targeted therapy, such as monoclonal antibodies or tyrosine kinase inhibitor, e.g. imatinib mesylate (Gleevec or Glivec).

Exemplary chemotherapeutics that can be encapsulated in the encapsulating material and delivered on-demand using the system described herein include, but are not limited to, cisplatin, carboplatin, mechlorethamine, cyclophosphamide, chlorambucil, ifosfamide, azathioprine, mercaptopurine, vinca alkaloids, taxanes (e.g. paclitaxel, docetaxel), type I topoisomerase inhibitors (e.g., camptothecins, irinotecan and topotecan), and type II inhibitors (e.g., amsacrine, etoposide, etoposide phosphate, and teniposide).

3. Antibiotics

The drug delivery system may contain an antibiotic. Suitable antibiotics include, without limitation, benzoyl peroxide, octopirox, erythromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate and cholate. The antibiotic can be an antifungal agent. Suitable antifungal agents include, but are not limited to, clotrimazole, econazole, ketoconazole, itraconazole, miconazole, oxiconazole, sulconazole, butenafine, naftifine, terbinafine, undecylinic acid, tolnaftate, and nystatin.

4. Antimicrobial Agents

The drug delivery system may contain an antimicrobial agent. Suitable antimicrobial agents include, but are not limited to, antibacterial, antifungal, antiprotozoal and antiviral agents, such as beta-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, metronidazole, pentamidine, gentamicin, kanamycin, lineomycin, methacycline, methenamine, minocycline, neomycin, netilmicin, streptomycin, tobramycin, and miconazole. Also included are tetracycline hydrochloride, famesol, erythromycin estolate, erythromycin stearate (salt), amikacin sulfate, doxycycline hydrochloride, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, nystatin, tolnaftate, clotrimazole, anidulafungin, micafungin, voriconazole, lanoconazole, ciclopirox and mixtures thereof.

E. Excipients

The drug delivery systems may contain one or more pharmaceutically acceptable excipients.

Suitable solubility enhancing agents include solvents such as water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones).

Suitable suspending agents include, but are not limited to, alginic acid, bentonite, carbomer, carboxymethylcellulose and salts thereof, hydroxyethylcellulose, hydroxypropylcellulose, microcrystalline cellulose, colloidal silicon dioxide, dextrin, gelatin, guar gum, xanthan gum, kaolin, magnesium aluminum silicate, maltitol, triglycerides, methylcellulose, polyoxyethylene fatty acid esters, polyvinylpyrrolidone, propylene glycol alginate, sodium alginate, sorbitan fatty acid esters, tragacanth, and combinations thereof.

The systems described herein may further contain a pH modifying agent including, but are not limited to, sodium hydroxide, citric acid, hydrochloric acid, acetic acid, phosphoric acid, succinic acid, sodium hydroxide, potassium hydroxide, ammonium hydroxide, magnesium oxide, calcium carbonate, magnesium carbonate, magnesium aluminum silicates, malic acid, potassium citrate, sodium citrate, sodium phosphate, lactic acid, gluconic acid, tartaric acid, 1,2,3,4-butane tetracarboxylic acid, fumaric acid, diethanolamine, monoethanolamine, sodium carbonate, sodium bicarbonate, triethanolamine, and combinations thereof.

Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

F. Dosage Forms Suitable for Injection

Suitable dosage forms for administration via injection include, but are not limited to, solution, suspensions, emulsions (e.g., microemulsions), liposomes, and nanoparticles.

Typical carriers for injection include, but are not limited to, sterile water, saline, phosphate buffered saline, glycerin, surfactants, such as TWEEN 80, polyethylene glycol, cyclodextrin, and combinations thereof.

II. Methods of Making the Drug Delivery Systems

Each component of the drug delivery system may be formed using standard methods. After the drug is encapsulated in the encapsulating material it can be administered to a patient with one or more of the precursor materials via injection. Typically, the system will contain two injectable precursor components that are injected via a double barrel syringe, or two separate syringes connected to each other via a t-connector or other suitable connector. Following injection, the precursor components mix and upon exposure to the appropriate conditions in vivo crosslink to form the drug depot with the drug encapsulating material (and drug encapsulated therein) contained within the drug depot.

In one embodiment, the drug encapsulating material also crosslinks to form the drug depot.

In the preferred embodiment, one or more of the precursor components contains microbubbles encapsulating a gas or gas mixture. In this embodiment, following injection and crosslinking at the desired site, the drug depot forms with the drug encapsulating material and microparticles contained therein.

In another embodiment, the drug depot is preformed prior to administration to the patient. In this embodiment, the various crosslinkable materials are crosslinked, typically in the presence of the encapsulating material containing the drug, and optionally in the presence of the microparticles, as well, to form the drug depot. The drug depot may be shaped in any desired shape that is suitable for implantation.

For drug depots that are hydrogels, the hydrogels may contain encapsulating material, optionally with microbubbles, in an amount of up to 20% by volume. Typically the volume of the hydrogel that contains the encapsulating material and/or microbubbles will not exceed 50%.

III. Disorders to be Treated

The drug delivery systems disclosed herein may be used to administer any pharmaceutically active agent, such as a drug or biologic, to a patient on-demand, i.e. as needed by the patient.

In one embodiment, the drug delivery systems are administered to a patient in need of alleviation from pain. Following administration of the drug delivery systems, the patient can determine when additional drug should be administered and control its release via the application of ultrasound to the patient.

In another embodiment, the drug delivery system is administered to a patient for the treatment of cancer. In this embodiment, the drug is typically one or more chemotherapeutics. This use of the drug delivery system allows for a patient to administer the chemotherapeutic at home after injection of the precursor components or implantation of the drug depot.

IV. Methods of Use for the On-Demand Drug Delivery System

In one embodiment, the precursor components are administered via injection to the patient. Following injection, the precursor components crosslink at the desired site to form the drug depot.

In another embodiment, the drug depot is preformed and is implanted in the patient at the desired site.

In a preferred embodiment, the patient administers the ultrasound to him or herself at the time and for the required duration to administered the desired dose of the drug or biologic. In another embodiment, a medical practitioner administers the ultrasound. Optionally, the ultrasound is focused at the site that the drug depot is located in the patient's body.

The encapsulating material will open up, thereby releasing the drug into the drug depot, which will erode and/or have pores with larger openings following ultrasound application. Then the drug depot will stop releasing drug when the ultrasound pulse is stopped. This step can be repeated to release drug or biologic as desired as long as the drug depot remains intact in the patient and as long as there is a sufficient amount of drug for release. For hydrogels, the drug depot will typically release drug following application of ultrasound for up to two weeks on-demand. For drug depots that erode more slowly, the drug depot may release drug following application of ultrasound for up to one year on-demand.

In one embodiment, one or more ultrasound transducers are applied to an external surface of the patient, preferably in close proximity to the site the drug depot is located. In another embodiment one or more transducers are inserted into the patient's body proximal to the location of the drug depot.

Figure 6:
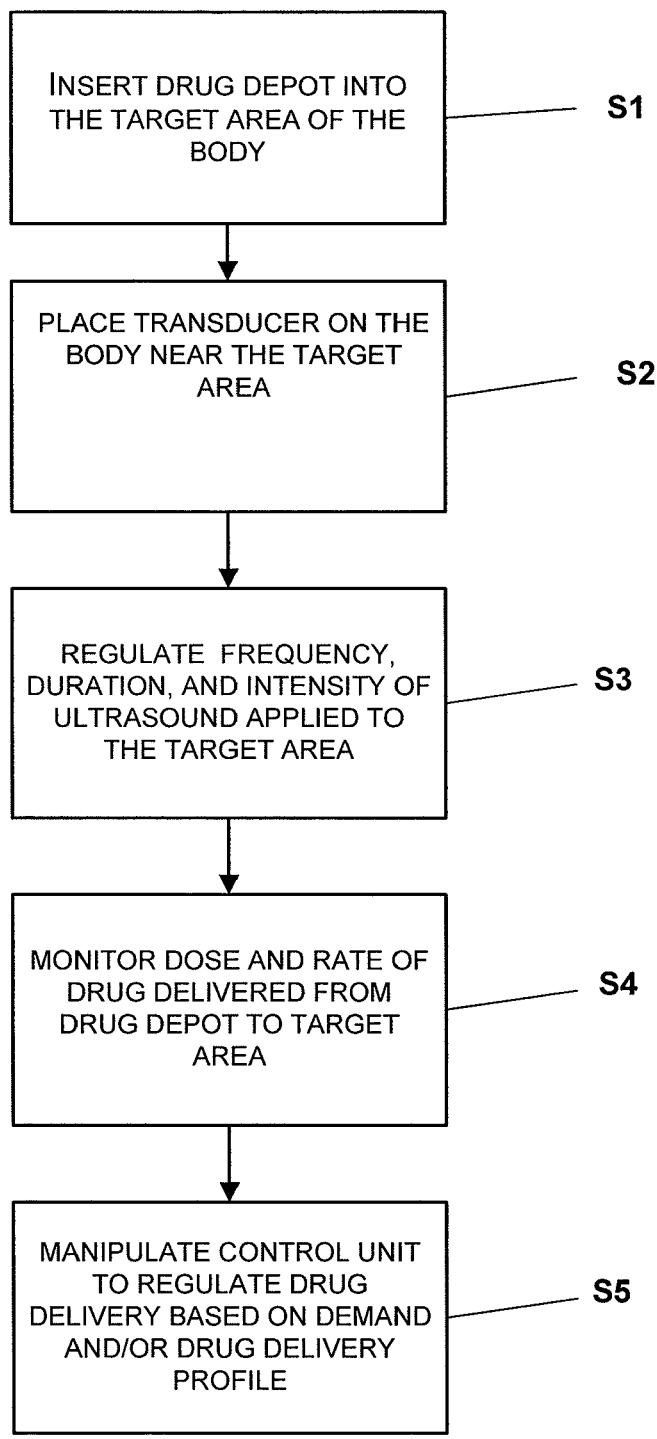
FIG. 6 is a process flowchart outlining a method of using the on-demand drug delivery device.

FIG. 6 shows a process flow chart outlining a method for using the drug delivery system. In a first step S1, the drug depot prepared according to any of the previously described methods is inserted into the body of the patient close to a targeted site within the body. In an alterative embodiment where the preparation of the drug depot forms part of the drug delivery device, step S1 includes injecting into the body one or more precursor components together with the encapsulating material containing the drug using syringes. The drug depot forms at the targeted site by crosslinking. Microbubbles can also be inserted into the body together with the precursor components. Next, one or more transducers are positioned (S2) on the outside of the body near the targeted area. The transducers are connected to a control unit (shown in FIG. 7) which controls the parameters of the ultrasound energy that the transducers deliver to the body of the patient and ultimately to the drug depot. Next, the user (patient, medical care person, administrator, etc.) can select in S3 the appropriate parameter (frequency, duration, intensity, etc.) of the ultrasonic energy that the transducers deliver to the patient so as to match the requirements needed by the various types of drugs to be delivered to the target site as well as the type of the target area. The dose and the rate of the drug delivered to the targeted site, as well as the intensity, frequency, and duration of the ultrasound delivered to the patient can be monitored (S4) using any applicable monitoring devices. The drug dose and rate of delivery to the targeted area can be repeatedly changed by the user to fit a particular medication demand and/or to fit a predetermined drug delivery profile. The amount of drug and/or the frequency of drug delivery to the targeted site can be changed by manually manipulating (S5) the settings on the control unit to change one or more parameters of the ultrasound energy applied to the patient.

Figure 7:
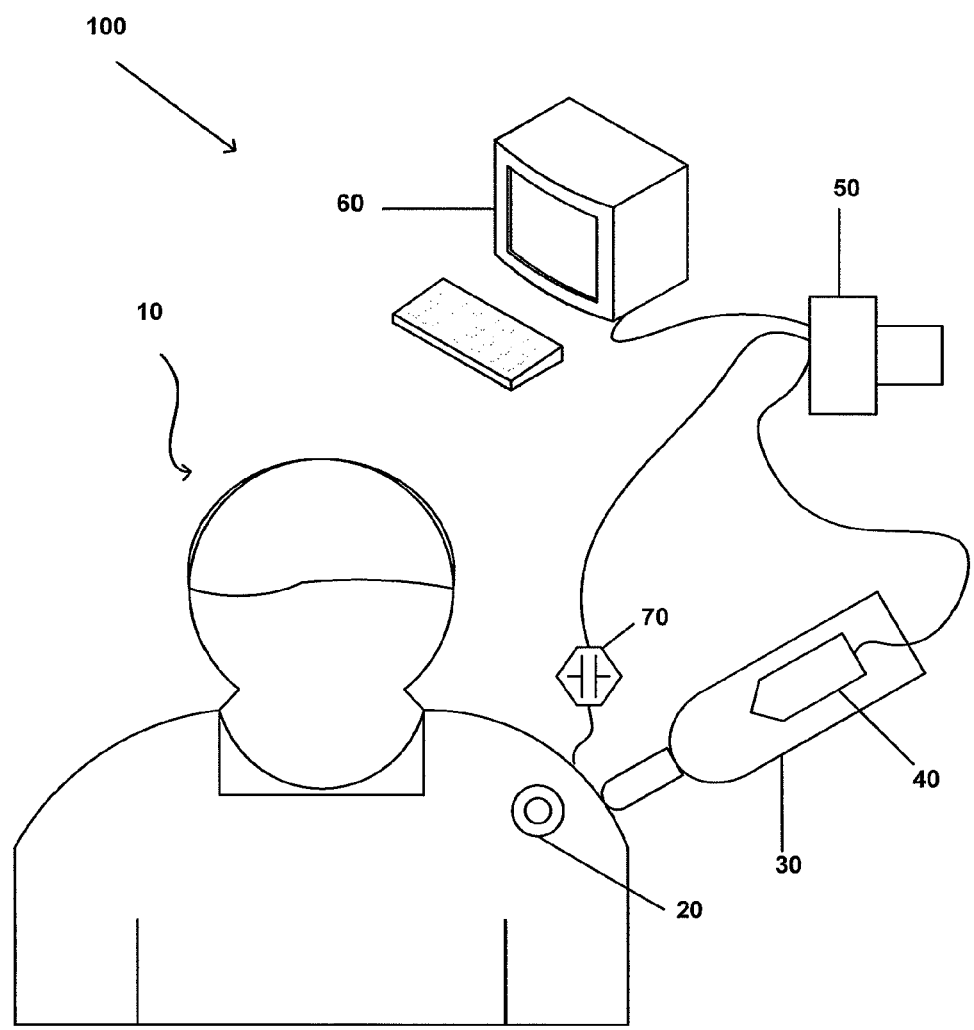
FIG. 7 is a diagram illustrating a method for on-demand drug delivery to a targeted area of a patient.

In an alternative embodiment, this process can be performed automatically using an external computer system (shown in FIG. 7). FIG. 7 illustrates an exemplary drug delivery system 100 which may regulate drug-delivery according to a demand signal or a feedback signal to achieve a controlled rate of delivery. A controller regulates the rate of delivery of pharmaceutical and/or biologic agents using ultrasound energy to a targeted site in the body of a patient 10. A drug depot 20 containing the pharmaceutical and/or biologic agents is administered to the patient via an insertion method described above. A coupling mechanism 30 may be placed on an external surface of the patient 10 near the targeted site so that ultrasound energy from a transducer 40 inserted into the coupling mechanism 30 can be focused onto the drug depot 20 which is positioned at or near the targeted site. The coupling mechanism 30 is shaped so as to accommodate contact with the body and to allow exposure to ultrasound energy generated by transducer 40. In an embodiment, the transducer 40 itself is shaped to avoid the need for a separate coupling mechanism. In embodiments, the coupling mechanism 30 and/or the transducer 40 is insertable into the body of the patient 10 and positioned near the drug depot 20. The transducer 40 may be positioned so as to deliver ultrasound energy to the drug depot 20. Responsively to the delivery of ultrasound, the drug depot 20 selectively releases the one or more agents onto the targeted area. The ultrasound may be regulated based on a demand for the medication, based on a predetermined drug delivery profile, and/or responsively to a feedback control loop with a control sensor such as one arranged to monitor the rate of the drug in the body such as by continuous sampling of blood or plasma or a rate of a toxin or other indicator of a condition in the body. The sensor may include a microfluidic assay chip or other device, for example.

Changing the dose and/or the rate of medication, or a target rate for a negative feedback control loop, to be delivered to the targeted area can be done by manually or automatically changing the intensity, duration and/or the frequency of the ultrasound energy delivered to the drug depot 20. An agent that regulates a detectable pathology that can automatically be measured and used to regulate the release of drug (e.g. lab on a chip detection of blood sugar with regulation of insulin release).

A control unit 50 controls the parameters, such as the intensity, duration and frequency of the ultrasound energy that the transducer 40 delivers to the drug depot 20. In an embodiment the control unit 50 can include a closed-loop feed-back controller configured to automatically adjust the electromagnetic field parameters of the ultrasound energy generated by the transducer 40 based on a feedback signal received from one or more sensors 70 (sensors detecting the agent for regulation of rate toward a control target or sensors detecting a pathology to adjust the rate or the target—or both) positioned adjacent and/or within the body of the patient 10. The sensor 70 detects the intensity of the ultrasound energy delivered to the drug depot 20 and the targeted area. In response to the detected signal from the sensor 70, the control unit 50 adjusts the ultrasound parameters.

The control unit 50 can further receive a signal from a drug sensing device (not shown) positioned outside or inside of the body of the patient 10 for detecting the amount of drug delivered to the target site or a measurable pathology. The drug sensor can include but is not limited to a polymer microchip inserted into the body near the targeted site to detect the drug dosage delivered to the site. Any other available external or internal sensing devices to detect drug dose delivered can be used. The control unit 50 can include a function generator to generate an electrical signal having a particular frequency and certain level according to a particular algorithm. The algorithm can be optimized for a particular application or treatment protocol. The control unit 50 can also be connected to an external computer processing system 60 so that the process of monitoring, controlling, and regulating of ultrasound energy delivered to the target area and adjacent tissue, and thus, monitoring, controlling, and regulating the amount and the rate of drug actually delivered to the targeted area can be automatically done. The drug dose and rate can be repeatedly changed and/or adjusted based on either a specific demand for the medication or a previously determined drug delivery profile saved in the computer processor 60.

The present invention will be further understood by reference to the following non-limiting examples.

EXAMPLES

Materials

Phenazine methosulfate, trypan blue, sodium chloride, methanol, chloroform, cholesterol, Dioctadecyldimethylammonium bromide (DODAB), CMC (medium viscosity), Dextran (100 kDa), adipic dihydrazide (ADH), 1-ethyl-3-[3-(dimethylamino)propyl]carbodiimide (EDC), hydroxybenzotriazole (HOBt), sodium periodate, ethylene glycol, tert-butyl carbazate (t-BC), sodium bicarbonate, sodium chloride, acetic acid and octyl β-D-glucopyranoside (OGP) were obtained from Sigma (St. Louis, Mo.).

HA (Mw=490 kDa and 1.4 MDa), 1,2-distearoyl-sn-glycero-3-phosphocholine (DSPC), and 1,2-distearoyl-sn-glycero-3-phosphatidylglycerol, sodium salt (DSPG) were purchased from Genzyme (Cambridge, Mass.).

Tert-butanol was purchased from Riedel-de Haën (Seelze, Germany).

Liposome Preparation

Liposomes were prepared by modified thin lipid film hydration. F. Szoka, Jr., D. Papahadjopoulos, Annu Rev Biophys Bioeng, 9: 467 (1980). Lipids were selected to produce relatively solid liposomes at 37° C. (phase transition temperatures, Tm; DSPC, DSPG=56° C.). DSPC:DSPG:cholesterol, negatively charged, DSPC:DODAB:cholesterol, positively charged, (molar ratio 3:1:2) and DSPC:cholesterol, neutral, (molar ratio 4:2) were dissolved in t-butanol and lyophilized. The lyophilized cake was hydrated with the dyes phenazine methosulfate (10 mg/mL) or trypan blue (10 mg/mL), at 55-60° C. The suspension was homogenized at 10,000 rpm with a ⅜" Mini-Micro workhead on a L4RT-A Silverson Laboratory Mixer (East Longmeadow, Mass.) for 10 minutes followed by ten freeze-thaw cycles. Excess free dye was removed by centrifugation (4000 rpm, 4° C. for 20 minutes) and replaced by 2 mL PBS and then dialyzed against PBS in 50 kDa molecular weight cut-off dialysis bags for 48 hours. Dye-free liposomes were prepared by the same procedure, omitting the dye.

Liposome Characterization

Liposomes were sized with a Beckmann Coulter Counter Multisizer 3 (Fullerton, Calif.). Zeta potentials were measured using Brookhaven Instruments Corporation ZetaPALS and ZetaPlus software (Holtsville, N.Y.). Liposome drug concentrations were determined following disruption of the liposomes with OGP.

Phenazine methosulfate and trypan blue were quantified by SpectraMax 384 Plus fluorometer (Molecular Devices, Sunnyvale, Calif.) at 387 and 607 nm, respectively.

Lipid concentrations were determined by colorimetry by the Bartlett assay. G. R. Bartlett, J Biol Chem, 234: 466 (1959).

Microbubble Preparation

Microbubbles were prepared using techniques described in Feshitan et al., Journal of Colloid and Interface Science, 329: 316 (2009).

Distearoyl-phosphatidylcholine (DSPC; Avanti Polar Lipids, Alabaster, Ala.) and polyoxyethylene-40 stearate (PEG40S; Sigma-Aldrich, St. Louis, Mo.) lipids were dissolved in chloroform at a molar ratio of 9:1, transferred to a scintillation vial, and evaporated with a steady nitrogen stream while vortexing for ten minutes followed by several hours under house vacuum. A 0.01 M solution of phosphate buffered saline (PBS) (Sigma-Aldrich) was filtered using 0.2-μm pore size polycarbonate filters (VWR, West Chester, Pa.). The dried lipid film was hydrated with filtered PBS and mixed with PEG40S to a final lipid concentration of 2.0 mg/mL, and sonicated with a 20-kHz probe (model 250A, Branson Ultrasonics; Danbury, Conn.) at low power (power setting dialed to 3/10; 3 Watts) above the main phase transition temperature of the phospholipid (~55° C. for DSPC).

Perfluorobutane gas (PFB; Fluoromed, Round Rock, Tex.) was introduced to the surface of the lipid suspension, and high power sonication (power setting dialed to 10/10; 33 Watts) was applied to the suspension for about 10 seconds at the gas-liquid interface to generate microbubbles.

The microbubble suspension was collected into 30-mL syringes (Tyco Healthcare, Mansfield, Mass.). Washing and concentrating by centrifugation was performed with a bucket-rotor centrifuge (model 5804, Eppendorf, Westbury, N.Y.), with a radius of approximately 16.1 cm from the center to the syringe tip, at 300 G for 5 minutes to collect the microbubbles from the suspension into a cake. The remaining suspension (infranate) was recycled for the next batch of microbubbles and resulting cakes were pooled and stored in sealed, 2-mL serum vials.

Microbubble Characterization

Microbubble size distribution was determined by laser light obscuration and scattering (Accusizer 780A, NICOMP Particle Sizing Systems, Santa Barbara, Calif.). 2-μL samples of each microbubble suspension were diluted into the 30-mL flask under mild mixing. Microbubble size distribution was also determined by the electrozone sensing method (Multisizer 3, Beckman Coulter, Opa Locka, Fla.). A 4-μL sample of microbubble suspension was diluted into a 60-mL flask and stirred continuously to prevent flotation-induced error. A 30 μm aperture (size range of 0.6-18 μm) was used for the measurements. All samples were measured in triplicate and analyzed for both number- and volume-weighted distributions.

Preparation of Hydrogels

To form the dextran-CHO/CMC-ADH hydrogel, dextran aldehyde was prepared as described in Ito, et al., Biomaterials 28:3418 (2007). 1.5 g dextran were dissolved in 150 mL of distilled water overnight, to which 802.1 mg of sodium periodate was added and stirred for 2 hours. 400 μL of ethylene glycol was added at 2 h to stop the reaction and was left to stir for an additional 1 h.

Hydrazide was prepared as described in Ito, et al., Biomaterials 28:3418 (2007). 0.5 g CMC was dissolved in 100 mL of distilled water, and reacted with 1.5 g of ADH in the presence of 240 mg EDC and 240 mg HOBt at pH 6.8 overnight at room temperature. The products were purified by exhaustive dialysis for 3 days, and then lyophilized. The purified product was freeze-dried and kept at 4° C.

The degree of fictionalization was quantified using 1H NMR for CMC-ADH and using hydroxylamine reaction for dextran-CHO. See Ito, et al., Biomaterials, 28: 975 (2007). In brief, 100 mg dextran-CHO was stirred in 25 mL of 0.25M hydroxylamine solution for 3 hours. The pH was measured and sodium hydroxide (0.1 M) was added in aliquots of 100 or 200 μl with the change in pH being recorded after every addition. A plot of dpH/dV against the total volume of NaOH was drawn, with the maximum peak corresponding to the number of moles of aldehyde groups present in the 100 mg of dextran-CHO.

To form hydrogel disks with liposomes and microbubbles, first the hydrogels were formed using a double-barreled syringe (Baxter: Deerfield, Ill.). The first syringe was loaded with 1 mL of 2.5% CMC-ADH solution in phosphate buffered saline (PBS). The second syringe contained 6% dextran-CHO mixed in PBS with different amounts of liposomes (0, 100, 200 and 500 □L) and different amounts of microbubbles (0, 200, 400 uL and 1 mL). In all cases, the final concentration of dextran-CHO was brought to 6% and the total volume in the second syringe was kept atl mL.

The two solutions were combined by injection into a rubber mold sandwiched between two slide glasses, resulting in a dextran-CHO/CMC-ADH hydrogel. The diameters and the thicknesses of the prepared hydrogels were 1.2 cm and 3.5 mm, respectively.

Hydrogel Characterization

Similar HA-ADH/HA-CHO (2.5%/2.5%) and HA-ADH/dextran-CHO (6%/2.5%) hydrogels were prepared, analyzed and compared to dextran-CHO/CMC-ADH (6%/2.5%) in terms of swelling ratio (%) and stability in vitro, in PBS and cell Medium (DMEM, Gibco) at 37° C. The time course of swelling of gel disks was measured gravimetrically as follows: the weight of the hydrogels after gelation time was measured up to 5 weeks after immersion in both solutions (every day for the first week and then every 3 days thereafter), by separating the portions of the hydrogels that remained intact from the degraded material by transferring intact disks into fresh wells of solution before each measurement.

The swelling ratio was calculated as the weight at a given time point divided by the initial weight of the hydrogel. Gelation time was measured as described in Ito, et al., Biomaterials, 28: 3418 (2007). Aqueous 0.1 mL CMC-ADH (2.5%) solution was mixed with aqueous 0.1 mL dextran-CHO (6%) solution with stirring at 155 rpm using a Corning model PC-320 hot plate/stirrer. The time until the mixture formed a gel was measured five times for each type of hydrogel, i.e. no additives, with liposomes (200=1.5% liposomes by volume), with microbubbles (800 μL=12.9% microbubbles by volume), and with liposomes with microbubbles (200 μL+800 μL) (1.5%+12.9% liposomes and microbubbles by volume) the measurements were done at 25° C. and 37° C.

In Vitro Drug Release Without Ultrasound Application

Liposome Formulation

One mL of liposomes or compounds in solution was inserted into the lumen of a SpectraPor 1.1 Biotec Dispodialyzer (Spectrum Laboratories, Rancho Domingeuz, Calif.) with a 50,000 MW cut-off. The dialysis bag was placed in a test tube with 12 mL PBS and incubated at 37° C. on a tilt-table (Ames Aliquot, Miles). At predetermined intervals, the dialysis bag was transferred to a new test tube with fresh PBS that was pre-warmed to 37° C. Concentrations of compounds were quantified as described above.

Drug Release from Gels

Disk-shaped dextran-CHO/CMC-ADH hydrogels with dye (trypan blue or phenazine methosulfate), either free in solution or encapsulated in liposomes (0, 100, 200, 300, 400 and 500 µL), and with or without microbubbles (0, 200, 400 and 800 µL), were prepared in a rubber mold sandwiched between two glass slides. The hydrogel disks were weighed and placed in 12-well plates with an insert for ease of gel transfer. 4 mL of phosphate buffered saline (PBS) was added to each well and the gels were incubated at 37° C. with constant rotation. Release medium was sampled (0.5 mL) at different time points and replaced with 4 mL of fresh PBS. The release samples were frozen until spectrophotometer analysis.

In Vitro Drug Release Following Ultrasound Application

A 20 KHz low-frequency ultrasonic processor (VC400, Sonics & Materials, Newtown, Conn.) was used. The ultrasonic probe (13 mm diameter) was immersed in a 12-well plate with insert. The hydrogel disks were placed into the inserts and submerged in a total of 4 mL solution per well. The probe was adjusted to rest at the top of the solution without directly contacting the hydrogels. Irradiation was conducted at a full duty cycle at varying intensities (0, 4, 6, 7, 8 and 10 W/cm2) and durations (0, 5, 7, 10 and 15 sec). The samples were kept in a temperature-controlled water bath, and its temperature was monitored (37° C.) throughout the experiment to prevent heat-induced liposomal drug release.

Cytotoxicity Assay

Microcomposite hydrogels (dextran-CHO/CMC-ADH, liposomes and microbubbles) were investigated in a human mesothelial cell line (CRL-9444: American Type Culture Collection (ATCC), Manassas, Va.) and macrophage cell line J774.A1 (TIB-67TM: ATCC) using the MTT assay (MTT kit, Promega G4100 Madison, Wis.). Briefly, mesothelial cells were grown and maintained in the complete growth medium (Medium199 with Earle's BSS, 0.75 mM L-glutamine and 1.25 g/L sodium bicarbonate supplemented with 3.3 nM epidermal growth factor, 400 nM hydrocortisone, 870 nM insulin, 20 mM HEPES and 10% fetal bovine serum (Gibco)) at 37° C. in 5% $CO_2$. Macrophages were grown and maintained in DMEM (Gibco, Carlsbad, Calif.) with 10% fetal bovine serum. Disk hydrogels, containing blank liposomes and microbubbles were placed in each well and floated in the culture medium 24 h after seeding the cells. MTT assay was performed 48, 72 and 96 hr and then every 7 days for up to 3 weeks after adding the hydrogels, for macrophages and mesothelial cells, respectively. Results were normalized to cells cultured without test compounds.

In Vivo Application of Dextran-CHO/CMC-ADH

Animals were cared for in compliance with protocols approved by the Massachusetts Institute of Technology Committee on Animal Care, in conformity with the NIH guidelines for the care and use of laboratory animals (NIH publication #85-23, revised 1985).

Subcutaneous Application

Male CD-1 mice (Charles River Laboratories, Wilmington, Mass.), (20-28 g) were anesthetized with 2-3% isoflurane in oxygen. The backs were shaved with an electric animal hair clipper and the shaved areas were cleaned with 70% ethanol solution. 0.1 mL of dextran-CHO/CMC-ADH hydrogels containing free trypan blue, or liposomes encapsulating trypan blue, with or without microbubbles, were injected from a double-barreled syringe (0.05 ml of 2.5% CMC-ADH in one syringe, 0.05 mL of 6% dextran-CHO with liposomes encapsulating trypan blue, with or without microbubbles, in the other syringe). Hydrogels with trypan blue liposomes and microbubbles were prepared as described above.

Ultrasound probe was applied to the shaven site above cold water, and the mice were exposed for a 1 minute cycle to ultrasound (6 W/cm², 10 sec pulse; 1 sec on/1 sec pulse off). Pictures were taken before and after ultrasound application, intensity of the color was analyzed using Adobe Photoshop pipette toll sampler CMYK color detection, color area was normalized to nearby area with no hydrogel in order to normalize the results to reduce the interference of light and the exposure time of the camera based on the operator. Animals were sacrificed for examination of the tissue reaction (6 and 14 days after injection). Tissues were processed for hematoxylin-eosin sections with standard techniques.

Rheological Testing

Rheological measurements were made with an AR-G2 controlled stress rheometer (Advanced Rheometer, TA Instruments, New Castle, Del.) using a 20-mm parallel plate geometry and 1.1 mm gap with adhesive-backed 600 grit silicon carbide sandpaper to ensure surface contact between the hydrogels and the bounding surfaces (McMaster-Carr, Elmhurst, Ill.). Dynamic oscillatory modes were used to measure the elastic (G'), loss (G") and complex moduli (G*). An initial strain sweep from 0.1-10% strain was performed for each gel at a frequency of 3 rad/s (18.8 Hz) to determine a range corresponding to the linear viscoelastic regime of our material (data not shown). A strain of 0.1%, was chosen within this range and all subsequent frequency sweeps were performed at this strain over a range of frequencies up to 15 rad/s (94.2 Hz), at 25° C. Four hydrogel types were tested for their relative mechanical characteristics: plain dextran-CHO/CMC-ADH (6%/2.5%) hydrogel, hydrogel with liposomes encapsulating trypan blue (200 µL liposomes), hydrogel with microbubbles (800 µL microbubbles) and hydrogel with 200 µL encapsulating liposomes plus 800 µL microbubbles. All sets of rheological data were collected twice using different blends of prepared microcomposite hydrogels. Variations of <10% were observed between the original and repeat moduli per gel type, confirming the high reproducibility of the rheological analysis.

Statistics

Data are presented as means±standard deviations (n=4 in release kinetics, cell work, and n=8 for in vivo studies). To take multiple comparisons into account, all statistical comparisons were done with the Tukey-Kramer test, using InStat software (GraphPad, San Diego, Calif.). A P-value<0.05 was considered to denote statistical significance.

Results

Hydrogel Preparation and Characterization

Hydrogels that cross-link in situ by formation of hydrazone bonds were evaluated with and without application of ultrasound. Their compositions are denoted as follows: hyaluronic acid, HA; carboxymethylcellulose, CMC; aldehyde modification, —CHO; adipic hydrazide modification, -ADH. Three hydrogels were tested: HA-CHO/HA-ADH, dextran-CHO/HA-ADH, and dextran-CHO/CMC-ADH. A polymer concentration of 6% for all dextran-CHO and 2.5% for all of the modified hyaluronic acid and carboxymethylcellulose components was used.

HA-CHO/HA-ADH and dextran-CHO/HA-ADH underwent visually obvious degradation in PBS and in cell culture medium by 5 and 10 days respectively, while dextran-CHO/CMC-ADH (6%/2.5%) maintained its shape in vitro for 4 weeks with no observable degradation. Following the application of low-frequency ultrasound (20 kHz), 1 hr after the formation of gels, in short, low-intensity pulses (10 sec each at 6 W/cm$^2$), the HA-ADH/HA-CHO (2.5%/2.5%) and dextran-CHO/HA-ADH (6%/2.5%) gels were macroscopically destroyed after 6 and 10 pulses, respectively.

in like-charged or neutral liposomes, but loading was unsuccessful in oppositely charged liposomes owing to particle aggregation. Data in Table 1 are presented as the mean±SD, where n=4.

Further experiments were conducted using dyes in liposomes with neutral charge or the same charge as the dye. Lipid concentrations for all formulations were in the range of 50-60 mg/mL.

TABLE 1

| Liposome type | Model drug | Drug Loading (mg/mL) | Lipid conc. (mg/ml) | Dye entrapment[g] (% of initial) | Mean diameter (μm) | Volume fractio (%)[h] | Zeta potential (mV) |
| --- | --- | --- | --- | --- | --- | --- | --- |
| DSPC:cholesterol 1::DODAB::3:2:1 (Positive charge) | Trypan blue[e] Phenazine methosulfate[d] | [f] 3.4 ± 0.02 | — 59 ± 5 | <2% 34 ± 2 | — 4.0 ± 2.5 | — 7.4 ± 0.63 | — +31 ± 2.1 |
| DSPC:cholesterol ::2:1 (Neutral) | Trypan blue[e] Phenazine methosulfate[d] | 3.2 ± 0.03 2.5 ± 0.04 | 60 ± 4 60 ± 3 | 32 ± 3 25 ± 4 | 4.2 ± 1.1 4.2 ± 1.1 | 7.5 ± 0.05 7.5 ± 0.37 | −0.4 ± 0.3 −0.9 ± 0.5 |
| DSPC:cholesterol:DSPG ::3:2:1 (Negative charge) | Trypan blue[e] Phenazine methosulfate[d] | 2.8 ± 0.04 — | 58 ± 3 — | 28 ± 4 <5% | 4.2 ± 1.1 — | 7.3 ± 0.34 — | −35.1 ± 1.3 — |

[d]Positively charged;
[e]Negatively charged;
[f]Not stable-aggregated;
[g]percentage of initial concentration;
[h]percentage of volume displaced in solution Dextran-CHO/CMC-ADH maintained its shape for 16 pulse applications. The dextran-CHO/CMC-ADH hydrogel also had the lowest swelling ratio: 50±7% compared to 220±14% for HA-CHO/HA-ADH and 120±23% for dextran-CHO/HA-ADH in PBS at 37° C. These findings suggested that dextran-CHO/CMC-ADH is the preferred hydrogel for this application. Consequently all subsequent experiments used dextran-CHO/CMC-ADH hydrogels.

$^1$H NMR spectra of CMC-ADH demonstrated the successful incorporation of ADH. The degree of modification was calculated from the ratio of the area of the peak for the N-acetyl-D-glucosamine residue of CMC (singlet peak at 2.0 ppm) to that for the methylene protons of the adipic dihydrazide at 1.62 ppm; 51.6% of the N-acetyl-D-glucosamine residues were modified. Analysis of aldehyde groups formed by the oxidation of dextran with hydroxylamine yielded a 33.1% degree of oxidation.

Liposome Preparation and Characterization

To produce liposomes suitable for hydrophilic drugs with various charges, lipids were prepared in three formulations containing (i) cholesterol with the neutral lipid DSPC, (ii) cholesterol and DSPC with the negatively charged DSPG, or (iii) cholesterol and DSPC with the positively charged DODAB (see Table 1). These lipids were combined in ratios previously determined to produce stable liposomes at 37° C. Epstein, et al., The AAPS Journal, 10: 505 (2008); Epstein-Barash, et al., Proceedings of the National Academy of Sciences of the United States of America, 106:7125 (2009).

The median volume-weighted diameter of the resulting multi-lamellar liposomes was approximately 4.0 μm for all three formulations. The liposomes are referred to as "neutral, "negative" and "positive" respectively based on measured median zeta potential charges of 0 mV, −35 mV and +31 mV.

Model Drug Encapsulation

Liposomes were loaded with two dyes used as model hydrophilic drugs: cationic phenazine methosulfate and anionic trypan blue. As shown below in Table 1, both "model drugs" achieved acceptable levels of encapsulation Liposomal Formulation Stability To identify the formulations with the lowest baseline (non-triggered) release, release kinetic studies were performed from dye-containing liposomes contained in dialysis membranes (50 kDa molecular weight cutoff) submerged in PBS at 37° C. Free phenazine methosulfate and free trypan blue in PBS were used as controls.

The results are shown in FIG. 1. Release of trypan blue was slightly slower from neutral liposomes than from negative liposomes (e.g. $p<0.05$ at 72 h). Similarly, the release of phenazine methosulfate was slightly slower from positively charged liposomes than from neutral liposomes (e.g. $p<0.05$ at 72 h, data not shown). Based on these results, only positive phenazine-methosulfate liposomes and neutral trypan blue liposomes were incorporated into hydrogels for further experimentation.

In all subsequent in vitro experiments, both trypan blue and phenazine-methosulfate were tested. Similar results were obtained for both. Representative data for trypan blue are provided.

Release Kinetics of Liposomes in Hydrogel

Dye-containing liposomes dispersed in dextran-CHO (400 μL liposomes per 1 mL 6% dextran-CHO) were mixed with an equal volume of 2.5% CMC-ADH via a double-barreled syringe in a rubber mold sandwiched between two glass slides. The resulting cross-linked hydrogel disks containing liposomes were weighed and placed into inserts submerged in 12-well plates filled with PBS at 37° C. to monitor release kinetics. Comparable concentrations of free dyes (1.36 mg/mL dye; the same amount as in 400 μL of liposomes) were incorporated into disks used as liposome-free controls. The release medium was sampled at predetermined time points and the gel inserts were transferred into plates with fresh PBS.

As shown in FIG. 1, incorporation into hydrogels slowed release of free dyes in solution (e.g. $p<0.01$ at 72 hr) and of liposome-encapsulated dyes (e.g. $p<0.001$ at 72 hr).

In all experiments, the final concentration of cross-linked polysaccharides was kept constant, irrespective of the varying amounts of other components added. (These were added as liquid suspensions to dried polymers.) Similarly, the concentration of dyes was maintained constant, whether the dyes were free or encapsulated.

Release Kinetics after Incorporation of Microbubbles

Microbubbles composed of neutral DSPC: PEG40S lipid monolayers with a molar ratio of 9:1 (DSPC:PEG40S) encapsulating perfluorobutane gas were incorporated into the composite gel disks (see Methods). Various properties of the microbubbles are summarized in below in Table 2. The data in Table 2 are presented as the mean±SD, where n=3. The median volume-weighted diameter of the microbubbles was approximately 4.0 μm (see Table 2).

TABLE 2

Characterization of Microbubbles

| Microbubble Composition (molar ratio) | Total Composition (particles/mL) | Volume Fraction (% volume displaced in solution) | Mean diameter (μm) |
|---|---|---|---|
| DSPC:PEG40S (9:1) | $8.4 \times 10^9 \pm 2 \times 10^9$ | 16.1 ± 7.6 | 2.3 ± 0.1 |

Hydrogel discs were made as described above to contain two different amounts of microbubbles (250 μL or 500 μL) and dye-containing liposomes (400 μL).

Release kinetics were monitored as described above. Incorporation of either amount of microbubbles did not change the baseline (untriggered) release kinetics of the dyes (data not shown).

Ultrasound-Triggered Release Kinetics

The effect of ultrasound on the release kinetics of dextran-CHO/CMC-ADH hydrogel discs formulated with both types of dye-containing liposomes, with or without microbubbles added, was investigated. Gel discs containing equal amounts of free dye were used as controls.

To apply the ultrasound pulse to each gel, the tip of an ultrasound probe was submerged 1.2 mm beneath the surface of the PBS but not in direct contact with the gels. At each time point, the release media were sampled, an ultrasound pulse was applied, and the release media were sampled again before the gel inserts were transferred to a fresh well of PBS in preparation for the next time point. All gels were incubated at 37° C. between time points.

The ultrasound was operated at 20 kHz, which was previously shown to be optimal for perturbing the lipid shells of liposomes. See, e.g., Schroeder, et al., Langmuir, 23:4019 (2007). As demonstrated in this example, ultrasound operated at 20 kHz also disrupts microbubbles.

Microbubbles in solution were exposed to 20 kHz ultrasound at pulse intensities of 4, 6 and 8 W/cm² for 10 sec, after which the size and number concentration were measured using a Beckmann Coulter Counter Multisizer 3. After the first pulse, the number concentration of the microbubbles was reduced by 57, 78 and 95% at pulse intensities of 4, 6 and 8 W/cm², respectively. After the second pulse, no microbubbles could be detected. The temperature of the PBS was monitored to ensure it remained 37° C. during ultrasound application.

Effect of Pulse Intensity on Release

Using a pulse duration of 10 sec, release was measured at pulse intensities of 4, 6, 8, and 10 W/cm². As shown in the bar graphs for FIG. 2A, these pulse intensities resulted in the visual destruction of the gels after the 18$^{th}$, 16$^{th}$, 12$^{th}$ and 2$^{nd}$ pulse, respectively, with a concurrent marked release of dye.

Of the intensities that did not result in rapid gel destruction, 8 W/cm² gave the greatest magnitude of release, but relatively poor reproducibility. Both intensities of 4 and 6 W/cm² provided reproducible release; however, the release at 6 W/cm² was higher than the release at 4 W/cm².

Effect of Pulse Duration on Release

Using a pulse intensity of 6 W/cm², release was tested at pulse durations of 5-15 seconds. The magnitude of % release correlated very closely with pulse duration ($R^2$=0.98) (see FIG. 2B, graph in "After" column), at least for the first few pulses. With 15-second pulses, the gels began to disintegrate after the 6$^{th}$ pulse (see FIG. 2B, graph in "Before" column). The gels were completely destroyed after the 9$^{th}$ pulse.

Effect of Liposome and Microbubble Concentrations on Triggered Release

Using 6 W/cm² in 10 sec pulses, increasing the liposomal content of the hydrogel discs from 100 to 500 μL dye-loaded liposomes per 1 mL dextran-CHO resulted in the same relative % release of the dye per pulse. However, absolute amount of dye released increased with liposomal content ($R^2$=0.996). For example, increasing from 200 to 400 μL dye-loaded liposomes per 1 mL dextran-CHO increased dye release from 0.141 to 0.279 mg/mL from the second pulse.

Increasing liposome content did not increase the number of cycles of sustained release that could be obtained.

200 μL of dye-loaded liposomes per 1 mL dextran-CHO were selected for further experimentation since this concentration yielded data that were in the optimal absorbance range of the spectrophotometer used in the experiment.

Figures 2A, 2B, 2C:
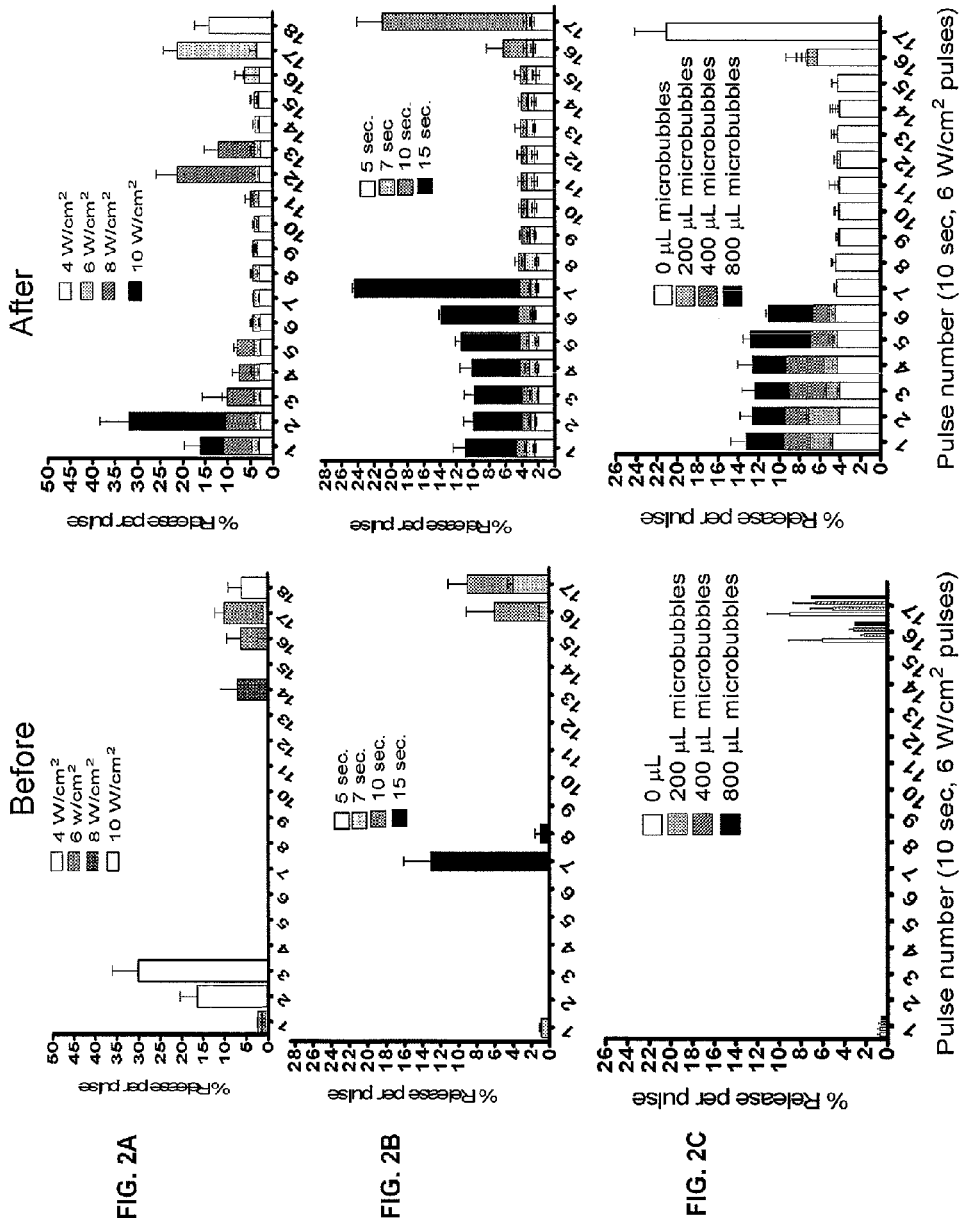
FIGS. 2A, B and C are bar graphs showing the effect of low-frequency ultrasound irradiation intensity (A) and pulse time (B) on in vitro release of trypan blue from 200 µL negative liposomes in dextran-CHO/CMC-ADH hydrogels at 37° C. For each parameter, the graphs provide dye release before (left panel) and after (right panel) each pulse. Data are means with standard deviations (n=4). For FIG. 2C, an irradiation intensity of 6 W/cm$^2$ and a pulse time of 10 sec were determined to be the optimal combination, and various microbubble concentrations (0, 200, 400 and 800 µL) were incorporated into the hydrogels and tested using those parameters.

The effect of adding different amounts of microbubbles to the hydrogels was investigated. As shown in FIG. 2C, increasing the amount of microbubbles in the hydrogel from 0 to 0.8 mL increased the number of cycles that showed enhancement of release. The addition of microbubbles lead to a linear increase in release magnitude ($R^2$=0.99) and the number of cycles over which that increase was seen: 200 μL of microbubbles caused release to increase from 4.5% for when no microbubbles were present to 7% (with 200 μL of microbubbles) and lasted for the first 2 pulses; 400 μL increased the release to 9% and lasted for 4 pulses, and 0.8 mL of microbubbles increased the release to 12.5% (an increase of 3.1 fold, p<0.001) that lasted for 6 pulses (see FIG. 2C).

The incorporation of microbubbles lead to more rapid depletion of dye in the gels, as seen in the fact that only the 0 and 200 μL groups showed triggered release at pulses 16 and 17, when the gels were disintegrating. All hydrogels released 3.8-4% of dye content per pulse during pulses 7 to 15, irrespective of microbubble loading (see FIG. 2C).

Effect of Liposome and Microbubble Incorporation on Hydrogel Properties

The effects of incorporating microbubbles and liposomes on the gelation time and viscoelasticity of the formulation was explored. Gel discs were prepared as described above (using neutral trypan blue liposomes), but with a stir bar rotating at ~150 rpm inside the plastic mold during injection. The gelation time was considered the time at which stir bar could no longer rotate inside the gels. The average gelation times for the various dextran-CHO/CMC-ADH gels is provided below in Table 3. Data are mean gelation time (sec)±SD, where n=5. The average gelation times for the dextran-CHO/CMC-ADH gel without additives was ~30 sec at 25° C., and was accelerated by the incorporation of liposomes and microbubbles, and by increasing the temperature from 25 to 37° C. (p<0.001 between all groups tested and between the groups at different temperatures).

TABLE 3

Gelation times of CMC-ADH 2.5%/DEX-CHO 6%, with additives

| Temp (° C.) | Gelation time (sec) | | | |
|---|---|---|---|---|
| | No additive | With liposomes | With microbubbles | With liposomes and microbubbles |
| 25 | 32.4 ± 0.6 | 25.6 ± 0.9 | 19.3 ± 0.5 | 11.4 ± 0.9 |
| 37 | 23 ± 0.7 | 17 ± 1.4 | 10.6 ± 0.55 | 6.4 ± 0.6 |

Figure 3A:
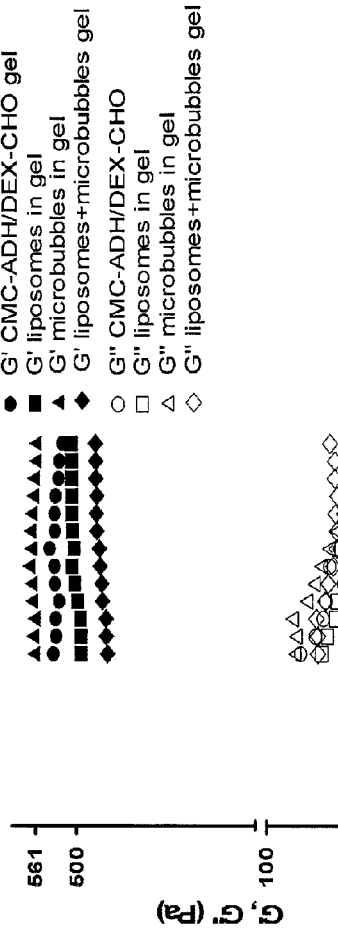
FIG. 3A is a graph of Elastic (G', filled symbols) and loss (G", unfilled symbols) moduli as a function of oscillation frequency for plain dextran-CHO/CMC-ADH (6%/2.5%) hydrogel with 200 µL liposomes encapsulating trypan blue, hydrogel with microbubbles and hydrogel with 1.5 encapsulating liposomes plus 800 microbubbles.

The viscoelastic properties were measured for plain dextran-CHO/CMC-ADH hydrogels, hydrogels with liposomes, and hydrogels with both liposomes and microbubbles. The results from these measurements are provided in FIGS. 3A and B. As shown in FIG. 3A, all samples exhibit similar elastic (G') and loss (G") moduli within the linear viscoelastic regime. All gels were predominantly elastic (G'>>G"), and the elastic moduli were essentially independent of frequency for the range tested. The viscous contribution to the total response is quantified by the loss tangent, tan δ=G"/G', which was small for all of the gels tested (tan δ<0.05).

Figure 3B:
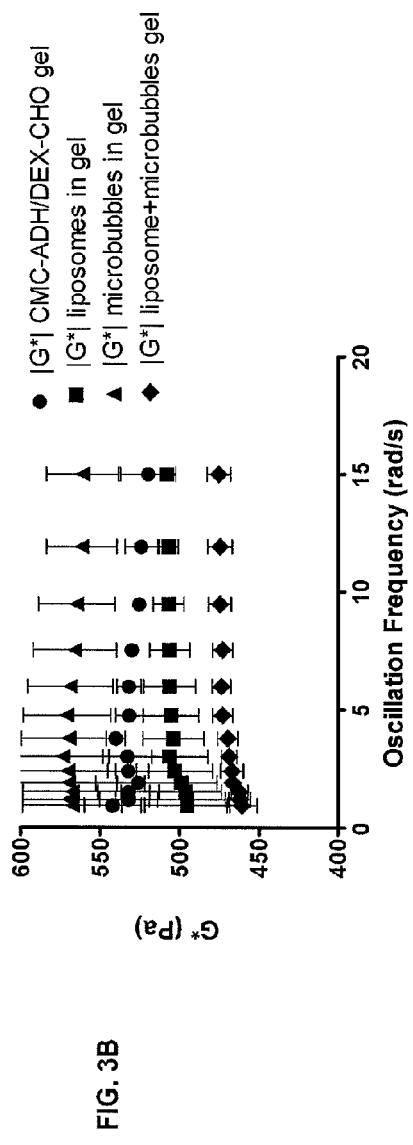
FIG. 3B is a graph of complex moduli G* as a function of oscillation frequency (rad/s) for the same hydrogels.

The standard deviation of the measurements is viewed by considering a single parameter, the magnitude of the complex modulus, $|G^*|=(G'2+G''2)^{1/2}$ These results are provided in FIG. 3B. A close comparison of |G*| values shows that the incorporation of microbubbles slightly increases the complex modulus, whereas the addition of liposomes (with or without microbubbles) decreases the complex modulus |G*|. While statistically significant, the differences are very slight (~10%) compared to the order of magnitude changes which may occur by varying the concentration or functionalization of the constituent polymers composing the hydrogel matrix.

Cytotoxicity Assay

Figure 4A:
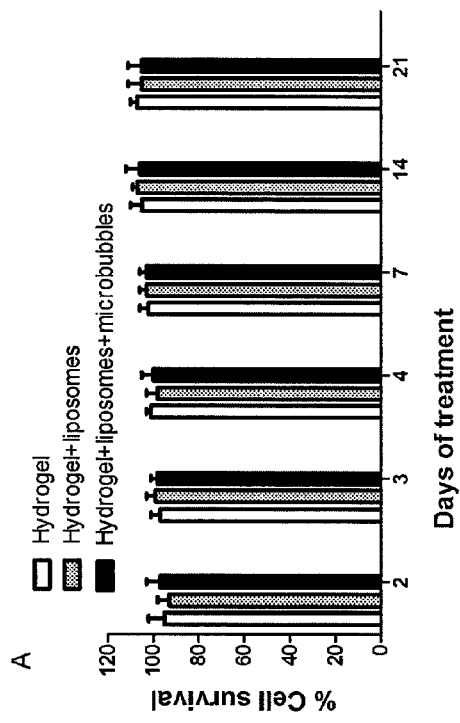
FIGS. 4A and B are bar graphs of the effect on cell viability (MTT assay) over time following exposure to dextran-CHO/CMC-ADH hydrogel (white bars), DSPC:DODAB:cholesterol-based liposomes (grey bars), and hydrogel-liposome-DSPC-based microbubble composites (black bars).
Figure 4B:
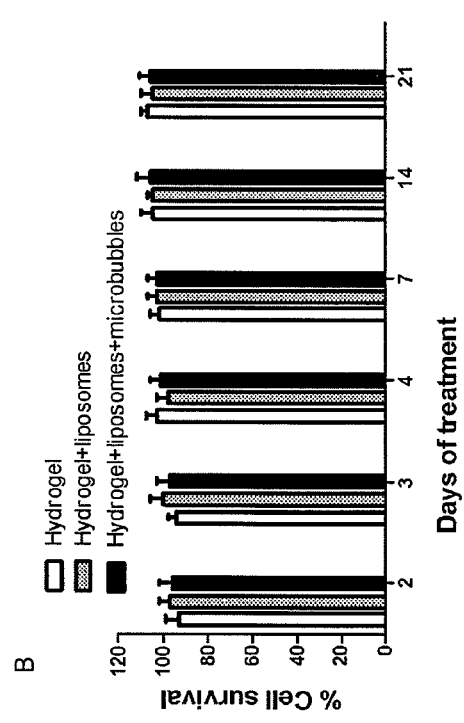
FIG. 4B shows the results for macrophages (J774.A1 cell line). Data are means with standard deviations (n=4).

Mesothelial (CRL-9444) and macrophage (J774.A1) cell lines were exposed to the hydrogel formulations, with or without liposomes and microbubbles, for up to 3 weeks with media changes every 3 days. Dye-free liposomes were used for this assay since the subject of inquiry was the delivery vehicle, not the model drug. The results of the cytotoxicity assay are depicted in FIGS. 4A and B. For the 3 weeks tested, both mesothelial (FIG. 4A) and macrophage (FIG. 4B) cell lines showed viability greater than 90% of that of cells not exposed to any formulation. Thus, the incorporation of liposomes and microbubbles into the hydrogels did not affect cell viability.

Ultrasound-Triggered Release in Vivo

To confirm the efficacy of the hydrogel system in vivo, composite gels with trypan blue, either free or in neutral liposomes (200 μL), with or without microbubbles (800 μL), were injected subcutaneously in CD-1 white mice. The injected region of the skin and the ultrasound probe were immersed in a water-filled cylinder, and the tip of the ultrasound was positioned at a distance less than 2 mm above but not in direct contact with the skin in order to avoid causing irritation or burns.

Figure 5:
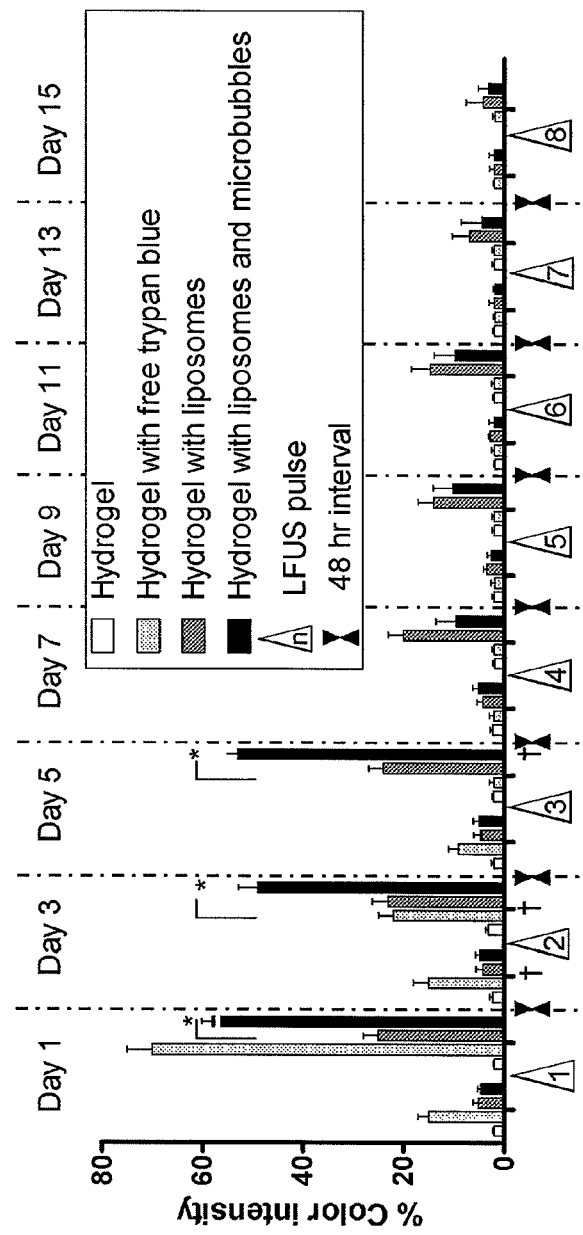
FIG. 5 is a bar graph of % color intensity for different dextran-CHO/CMC-ADH hydrogels injected subcutaneously into mice, before and after administering low frequency ultrasound (LFUS). The in vivo LFUS-triggered release profile of trypan blue from neutral liposomes suspended with microbubbles in dextran-CHO/CMC-ADH hydrogels injected subcutaneously into mice. "% color intensity" is a measure of the intensity of blue color obtained from pictures of the injection site taken before and after each pulse. Data are means with standard deviations (n=8). *$p<0.001$. †=indicate the time points of immediately before the second pulse, immediately after the second pulse, and 24 h after the third pulse, which are discussed in the Examples section.

The appearance of trypan blue in the usually white-tan mouse skin was evaluated to determine the in vivo feasibility of controlling the dye release as an on-and-off, on-demand application. To quantitate the intensity of blueness before and after each pulse of the ultrasound, digital pictures of the injection site were taken, and the intensity of the released blue in the center of the injection site was analyzed as described above (see Methods). These results are shown in FIG. 5.

The skin of mice injected with hydrogels containing free trypan blue developed bluish discoloration within 20 min after injection, even without the application of ultrasound. The blue became more intense with the application of a first 1 min ultrasound pulse of 1 min. (This pulse duration was developed empirically, to avoid causing burns, and consisted of six 10-sec bursts separated by 1-sec off Pulses were administered 48 hr apart.) Skin color returned to baseline after 24 hr. A second 1 min pulse at 48 hr caused the blueness to return; the color was gone by 24 hr thereafter. No dye could be detected after a third pulse.

In contrast, hydrogels containing trypan blue in liposomes both with and without microbubbles showed minimal discoloration of the skin for more than 2 weeks in the absence of ultrasound application. With application of ultrasound, dye-containing liposomes showed on-demand release for two weeks. Twenty-four hr after each pulse the intensity of the dye on the skin returned to a background level of 5%. An increase in released dye after insonation was seen for 6 pulses, after which it was hard to detect visually.

The addition of microbubbles resulted in a visually higher release of trypan blue in response to insonation. For example, after the first pulse, the measured blue intensity was 23±3% for hydrogels with liposomes, and 56±2.7% for hydrogels with liposomes and microbubbles (p<0.001).

Necropsy

Separate groups of hydrogels were injected subcutaneously, and excised on day 6, 24 h after the third pulse. The injection sites were excised from all other animals on day 14. In all cases, the hydrogels were still localized at the site of injection. Hydrogels containing liposomes were very blue in color, in contrast to the hydrogels containing free-dye, which were almost clear. Tissue reaction was mild, with little matting or apparent inflammation. Light microscopy revealed a mild-to-moderate inflammatory reaction, with some foamy macrophages (suggesting ingestion of the formulation) and some centralized nuclei in muscle cells, suggesting mild muscle injury. No difference could be observed between the tested groups.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

While the preferred forms of the disclosed subject matter have been disclosed, it will be apparent to those skilled in the art that various changes and modifications may be made that will achieve some of the advantages of the disclosed subject matter without departing from the spirit and scope of the disclosed subject matter. It will be apparent to those reasonably skilled in the art that other components performing the same function may be suitably substituted. Although specific embodiments of the disclosed subject matter have been described, various modifications, alterations, alternative constructions, and equivalents are also encompassed within the scope of the disclosed subject matter.

What is claimed is:

1. A composition implantable in living tissue as a drug depot for delivering a therapeutic agent to a targeted area of a subject to be treated over a period of time, the composition comprising:

a protective medium composed of a hydrogel and configured to degrade in response to application of ultrasound energy;

an agent encapsulated in an encapsulating material, the encapsulating material being suspended in the protective medium; and a plurality of microbubbles suspended in the protective medium, each of the microbubbles having an envelope of material that is different from said protective medium and encapsulating a respective gas core, wherein the composition is configured to permit the regulation of the release of the agent from the protective medium by selective application of the ultrasound energy to the protective medium, the hydrogel is capable of maintaining the agent and the microbubbles in close proximity to each other, the microbubbles are present at a concentration effective to disrupt the encapsulating material of the agent to release the agent into the protective medium, and the protective medium is configured to permit the release of the agent from the protective medium by the selective application of the ultrasound energy.

2. The composition of claim 1, wherein the release of the agent from the protective medium is triggered by exposure to a biocompatible dose of the ultrasound energy delivered to the targeted area.

3. The composition of claim 2, wherein the rate of the release of the agent from the protective medium is responsive to a dose and a rate of the ultrasound energy applied thereto.

4. The composition of claim 3, wherein the dose and rate of agent release may be regulated responsively to a parameter of the applied ultrasound energy, the parameter including at least one of intensity, frequency and duration.

5. The composition of claim 4, wherein the agent includes a pharmaceutical agent and/or a biologic agent.

6. The composition of claim 5, wherein the degradation of the hydrogel changes according to changes in the intensity, frequency and duration of the applied ultrasound energy.

7. The composition of claim 6, wherein the encapsulating material is one of a lipid vesicle, a microparticle, a nanoparticle, and a particle having a diameter greater than 500 microns.

8. The composition of claim 2, wherein the release of agent may be induced by the application of biocompatible amounts of the ultrasound energy by means of a plurality of transducers focused at a target area where the protective medium is located in a living host without injuring the living tissue of the living host.

9. The composition of claim 1, wherein the envelope of each microbubble is a lipid monolayer structure.

10. The composition of claim 1, wherein the envelope of each microbubble is a lipid bilayer structure.

11. The composition of claim 1, wherein the encapsulating material is of a substance that is different from the protective medium.

12. The composition of claim 1, wherein said agent includes a therapeutic substance.

13. The composition of claim 1, wherein said agent includes a drug.

14. The composition of claim 1, wherein said agent includes a diagnostic substance.

* * * * *

UNITED STATES PATENT AND TRADEMARK OFFICE
CERTIFICATE OF CORRECTION

| | | |
|---|---|---|
| PATENT NO. | : 10,010,709 B2 | Page 1 of 1 |
| APPLICATION NO. | : 13/515764 | |
| DATED | : July 3, 2018 | |
| INVENTOR(S) | : Daniel S. Kohane, Hila Epstein-Barash and Mark A. Borden | |

It is certified that error appears in the above-identified patent and that said Letters Patent is hereby corrected as shown below:

In the Specification

Please insert the following heading and paragraph at Column 1, Line 14:
--STATEMENT REGARDING FEDERALLY SPONSORED RESEARCH
This invention was made with government support under Grant number GM073626, awarded by The National Institutes of Health. The government has certain rights in this invention.--

Signed and Sealed this
Thirteenth Day of December, 2022

Katherine Kelly Vidal
*Director of the United States Patent and Trademark Office*